United States Patent
Lin et al.

(10) Patent No.: US 8,046,058 B2
(45) Date of Patent: Oct. 25, 2011

(54) HEART BEAT SIGNAL RECOGNITION

(75) Inventors: Szming Lin, San Jose, CA (US); Thomas Ying-Ching Lo, Fremont, CA (US)

(73) Assignee: Salutron, Inc., Fremont, CA (US)

( * ) Notice: Subject to any disclaimer, the term of this patent is extended or adjusted under 35 U.S.C. 154(b) by 1110 days.

(21) Appl. No.: 11/837,166

(22) Filed: Aug. 10, 2007

(65) Prior Publication Data

US 2009/0043216 A1    Feb. 12, 2009

(51) Int. Cl.
*A61B 5/04*    (2006.01)
(52) U.S. Cl. .................. 600/509; 600/455; 600/502
(58) Field of Classification Search .......... 600/450–505, 600/508–509
See application file for complete search history.

(56) References Cited

U.S. PATENT DOCUMENTS

| 6,024,705 A | 2/2000 | Schlager |
| 2006/0064037 A1 | 3/2006 | Shalon |
| 2007/0021679 A1 | 1/2007 | Narayan |
| 2007/0276270 A1 * | 11/2007 | Tran .............................. 600/508 |

OTHER PUBLICATIONS

International Search Report and Written Opinion of the International Searching Authority, dated Nov. 10, 2008, PCT Appl. No. PCT/US2008/072487, filed Aug. 7, 2008.

Bursa, et al., The Use of Ant Colony Inspired Methods in Electrocardiogram Interpretation, an Overview. NiSIS 2006 2nd Annual Symposium, Puerto de la Cruz, Tenerife, Spain, Jan. 12, 2006.
Rabiner, "A Tutorial on Hidden Markov Models and Selected Applications in Speech Recognition", Proceedings of the IEEE, vol. 77, No. 2, Feb. 1989, pp. 257-286.

* cited by examiner

*Primary Examiner* — Carl H Layno
*Assistant Examiner* — Paula J Stice
(74) *Attorney, Agent, or Firm* — Vierra Magen Marcus & DeNiro LLP

(57) ABSTRACT

A subject's heart rate is determined. A heart rate monitor receives a Doppler signal reflected from an artery of a target, performs demodulation and heart beat recognition techniques to determine a set of features in each frame of the signal. Pattern classification is performed to determine if the extracted feature sequence is associated with heart beats. The pattern classification may include finding the optimal state sequence by calculating the probability of each allowable state sequence based on the extracted feature sequence and heart beat models or additional noise models. Or, a heart beat candidate is determined using frame energy and dynamic thresholding followed by computing the probabilities between the feature sequence and each stored heart beat model or additional noise models. Or, heart beat candidates are determined using frame energy and dynamic thresholding which compute the similarity between the feature sequences and each of the stored heart beat templates.

41 Claims, 15 Drawing Sheets

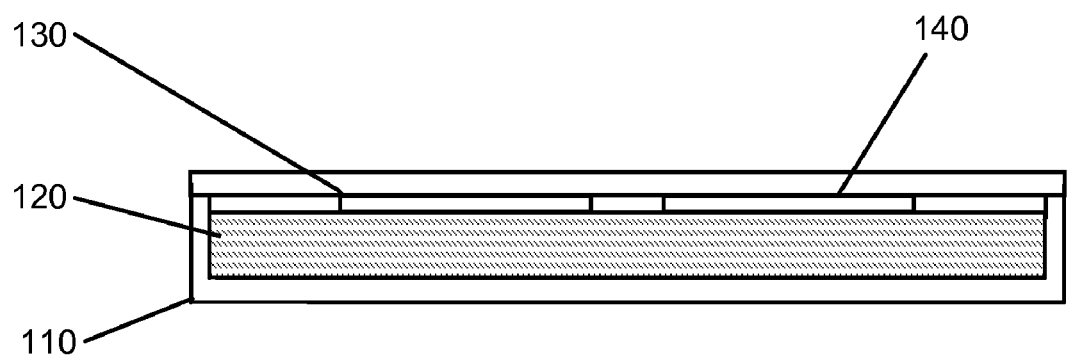
Figure 1 – Prior Art

HEART BEAT SIGNAL RECOGNITION

BACKGROUND

Measuring heart and pulse rates in living subjects has become a valuable tool during physical exercise and for health monitoring. The heart rate and pulse rate of a subject are related. Heart rate may be defined as the number of heart contractions over a specific time period, usually defined in beats per minute. A pulse is defined as the rhythmical dilation of a vessel produced by the increased volume of blood forced through the vessel by the contraction of the heart. Since heart contractions normally produce a volume of blood that can be measured as a pulse, heart rate and pulse rate are ideally the same. However, a pulse rate may differ from the heart rate during irregular heart beats or premature heart beats. In this case, a heart contraction may not force enough blood through a blood vessel to be measured as a pulse.

A pulse rate is measured by counting the rate of pulsation of a subject's artery. The heart rate is measured by sensing the electrical activity of the heart based on electrocardiograms (for example EKG or ECG). Individuals who want to increase their endurance or performance may wish to exercise while maintaining target heart rates. Conversely, subjects with a history of heart disease or other heart related condition should avoid exceeding a certain heart or pulse rate to reduce unnecessary strain on their heart.

Most subjects that require continuous heart rate readings choose a monitor that requires a chest strap. Though they provide heart rates continuously, chest straps are cumbersome and generally undesirable to wear. In addition to chest strap solutions, portable patient monitors (e.g., vital signs monitors, fetal monitors) can perform measuring functions on subjects such as arrhythmia analysis, drug dose calculation, ECG waveforms cascades, and others. However, such monitors are usually fairly large and are attached to the subject through uncomfortable wires.

Pulse rate can be measured at the wrist. The shallow depth of the radial artery in the wrist offers a number of advantages for achieving continuous pulse detection at the wrist. Prior sensors that monitor pressure pulses in the wrist have not been effective. Pressure pulses are attenuated by the tissues between the artery and the sensor. Most of the high frequency signal components are lost because of the attenuation. Additionally, muscle movement may create substantial noise at the pressure sensors. The low frequency noise signals make it very difficult to reliably identify low frequency blood pressure pulses.

Ultrasonic monitors using sonar technology were developed to overcome noise signal problems. Ultrasonic monitors transmit ultrasonic energy as a pulse signal. When a power source drives a transducer element, such as a piezoelectric crystal, to generate the pulse signal, the ultrasonic pulse signal is generated in all directions, including the direction of the object to be measured such as a blood vessel. The portion of the ultrasonic pulse signal reaching the vessel is then reflected by the vessel. When the blood vessel experiences movement, such as an expansion due to blood flow from a heart contraction, the reflected pulse signal experiences a frequency shift, also known as the Doppler shift.

When either the source of an ultrasonic signal or the observer of the sonar signal is in motion, an apparent shift in frequency will result. This is known as the Doppler effect. If R is the distance from the ultrasonic monitor to the blood vessel, the total number of wavelengths λ contained in the two-way path between the ultrasonic monitor and the target is 2R/λ. The distance R and the wavelength λ are assumed to be measured in the same units. Since one wavelength corresponds to an angular excursion of 2π radians, the total angular excursion Φ made by the ultrasound wave during its transit to and from the blood vessel is 4πR/λ radians. When the blood vessel experiences movement, R and the phase Φ are continually changing. A change in Φ with respect to time is equal to a frequency. This is the Doppler angular frequency $W_d$, given by $$W_d = 2\pi f_d = \frac{d\Phi}{dt} = \frac{4\pi}{\lambda}\frac{dR}{dt} = \frac{4\pi V_r}{\lambda}$$

where $f_d$ is the Doppler frequency shift and $V_r$ is the relative (or radial) velocity of target with respect to the ultrasonic monitor.

The amount of the frequency shift is thus related to the speed of the moving object from which the signal reflects. Thus, for heart rate monitor applications, the flow rate or flow velocity of blood through a blood vessel is related to the amount of Doppler shift in the reflected signal.

A piezoelectric crystal may be used both as the power generator and the signal detector. In this case, the ultrasonic energy is emitted in a pulsed mode. The reflected signal is then received by the same crystal after the output power source is turned off. The time required to receive the reflected signal depends upon the distance between the source and the object. Using a single crystal to measure heart rates requires high speed power switching due to the short distance between source and object. In addition, muscle movement generates reflections that compromise the signal-to-noise-ratio in the system. The muscle movement noise has a frequency range similar to the frequency shift detected from blood vessel wall motion. Therefore, it is very difficult to determine heart rates with this method. The advantage of this approach, however, is low cost and low power consumption.

In some ultrasonic signal systems, two piezoelectric elements are used to continuously measure a pulse. The two elements can be positioned on a base plate at an angle to the direction of the blood. In continuous pulse rate measurement, the Doppler shift due to blood flow has a higher frequency than the shifts due to muscle artifacts or tissue movement. Therefore, it is more feasible to separate pulse signals from muscle artifacts using ultrasound Doppler technology than other methods such as pressure, infrared, RF and other sensing techniques. The disadvantages of continuous mode over pulsed mode are higher cost and more power consumption.

Although blood flow has a higher frequency shift than muscle artifacts for a subject at rest, this difference is minimized when a subject is exercising. When muscle mass moves at a higher speed, for example during exercise such as running, the frequency of the noise generated by the muscle mass is closer to the blood flow frequency. This is because the muscle mass may be moving at a similar speed as the blood flow. As a result, the muscle noise signal and blood flow signal will overlap in the same frequency band.

Most prior heart rate monitors determine a subject's heart rate by calculating a time period between two or more detected heart beats. When monitoring a subject, it can be difficult to determine the difference between a heart beat and noise which occurs within the body of the subject. When noise is mistaken for a heart beat, the heart rate calculated as a result of the noise becomes inaccurate. This problem is compounded when a subject being monitored is active, and the level and variations of noise increase within the subject due to increased activity. It would be advantageous to more accurately determine a heart rate within a subject.

SUMMARY

The present technology determines a subject's heart rate using heart beat recognition techniques. A heart rate monitor receives a signal reflected from an artery of a target. The signal is processed to extract features using filter bank, linear predictive method or other signal processing methods. In some embodiments, the monitor system may need to find the heart beat signal in a background of noise or other acoustic interference. The extracted features are processed using pattern recognition techniques to determine if the signal contains a true heart beat.

The received signal data is divided into frames, and features are extracted from each frame signal. The extracted features from each frame are processed and/or compared to heart beat models and/or heart beat features for one or more heart beats and optionally noise. Based on the processing, including any comparisons, a determination is made as to whether the frame signal data contains a heart beat candidate or not. If so, the signal is processed further to determine if it contains a true heart beat.

In some embodiments, the signal reflected from a subject's artery is divided into frames. Heart beat recognition techniques are then performed on data for each frame (frame signal data) to determine features for the portion of the signal within the frame. Features may include LPC coefficients, formants, cepstral coefficients, Mel frequency cepstral coefficients (MFCC), perceptual linear prediction (PLP), signal energy, and other values derived from the signal. Once a set of features is extracted for a set of consecutive frames, the set of features is processed to determine a match with a library of stored heart beat and noise models. The match determination can indicate whether the signal is associated with a true heart beat or some other source, such as noise. Once a true heart beat is detected, the heart rate is updated based on the detected heart beat and displayed for a user.

Each heart beat model characterizes the features of a possible heart beat pattern. Each noise model characterizes the features of certain noise pattern. In some embodiments, these models are built using the hidden Markov model (HMM) approach.

An embodiment may extract a set of heart beat features from a heart beat signal. A set of heart beat coefficients may then be generated from the set of heart beat features. The set of heart beat coefficients can then be processed against one or more heart beat models. A determination is then made as to whether the set of heart beat coefficients represents a true heart beat. The determination may be based on the comparison with each of the one or more heart beat models.

This summary is provided to introduce a selection of concepts in a simplified form that are further described below in the description. This summary is not intended to identify key features or essential features of the claimed subject matter, nor is it intended to be used as an aid in determining the scope of the claimed subject matter.

BRIEF DESCRIPTION OF THE DRAWINGS

FIG. 1 is an example of a heart rate monitor of the prior art.

DETAILED DESCRIPTION

Figure 2A:
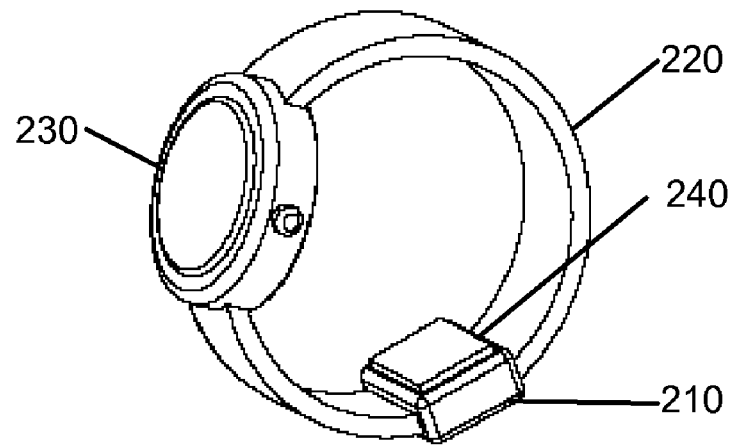
FIG. 2A is an example of a wrist worn heart rate monitor.

A heart rate of a subject is determined using heart beat recognition techniques. A heart rate monitor transmits a signal towards a target subject and receives a signal reflected from an artery of the target subject. The reflected signal may contain a heart beat and/or noise and is processed to determine if the signal data is recognized as a heart beat. Processing may include extracting and deriving features from the signal and processing the extracted features. The extracted features may be compared to other features, processed by a model, and/or otherwise processed to determine whether the features are associated with a recognized heart beat. In some embodiments, the features are processed to determine the probability that the features are associated with a heart beat. Using various sound recognition techniques, the present system may recognize heart beats contained in signals which also contain noise due to a subject exercising or other sources. If the extracted features are determined to be associated with a heart beat, the heart rate for the subject is updated with information for the heart beat and may be reported.

Feature extraction begins with dividing the reflected signal into frames. The signal data within a frame is called frame signal data. Two consecutive frames can be overlapping or non-overlapping. In some embodiment, a frame size is 45 ms and the overlap between two consecutive frames is 30 ms. Signal processing techniques are performed to extract one or more heart beat features from frame signal data of each frame, including LPC coefficients, formants, cepstral coefficients, Mel Frequency Cepstral Coefficients (MFCC), signal energy and other values. Processing a sequence of frames results in generation of a feature sequence. Pattern comparison techniques are then performed using the feature sequence to determine if the extracted feature sequence is associated with one or more heart beats.

Pattern recognition may be performed in several ways. Example pattern recognition techniques suitable for use with the present system and discussed herein include template comparison, discrete Hidden Markov Models (HMM), and continuous HMMs using a Viterbi search algorithm. Each technique may access stored data associated with heart beats and noise while processing the signal frame data. The stored data is used to determine whether the received signal should be characterized as a heart beat or noise based on a selected model or template associated with either a heart beat or noise. For example, if a feature sequence extracted from the reflected signal is determined to have a highest probability match with a heart beat template within several heart beats and noise templates, the reflected signal can be considered to contain a heart beat. These three pattern recognition techniques are intended only as an examples, and are not intended to limit the scope of the present heart beat sound recognition system. For example, other pattern recognition techniques like neural network or SVM (Support vector machine) may also be used.

A pattern recognition technique that utilizes template comparison involves comparing features extracted from signal frame data to one or more feature templates for heart beats and/or noise. In this technique, the system divides the signal into frames and determines a frame energy for each frame. Potential heart beat data is selected based on a comparison of the frame energy with an energy threshold selected to be higher than the background noise energy. In some environments, the energy threshold value may be dynamically determined to address changing background noise levels based on recent heart beat and noise energy statistics.

Once potential heart beat data is identified, one or more features are extracted from the frame signal data and compared against one or more heart beat and/or noise templates. The templates may be a feature sequence developed from the monitored subject, other subjects, computer models, or in some other manner. The comparison between the extracted feature sequence and the template measures the spectral difference, or spectral distortion or spectral-distance. In some embodiments, when the extracted feature sequence has a different period (or number of frames) from a heart beat template, a dynamic programming method such as dynamic time warping (DTW) may be used to measure the dissimilarity between the extracted feature sequence up to frame x and the template up to frame y, where X and Y are the maximum number of frames in the extracted feature sequence and the template, respectively. After comparing the extracted feature sequence to each template, the template associated with the smallest distortion or difference is selected, and the frame signal data or feature set extracted from the data are characterized according to the particular template. For example, if the smallest difference is associated with a heart beat template, the signal associated with the extracted features is considered a heart beat candidate.

Another pattern recognition technique suitable for use in the present system is HMM model comparison using discrete HMM techniques. When using a discrete HMM technique for pattern recognition, the reflected signal is divided into frames, the frames are filtered (e.g., with an energy threshold filter), and a set of features is extracted from frame signal data. The set of extracted features (feature sequence) is identified as an observation sequence and processed by one or more heart beat HMM models and noise HMM models. Each HMM model characterizes the features of one or more frames of a possible heart beat pattern or a noise pattern. A probability of the observation sequence matching a particular model is calculated by each HMM model. The highest probability is selected and if the highest probability matches a heart beat model, the candidate feature sequence is associated with a heart beat. If the highest probability matches a noise model, the candidate feature sequence is identified as associated with noise or other source. In some embodiments, if highest probability does not meet a minimum value, the extracted features for the selected frame are discarded and not used to update a subject's heart rate.

In template comparison and discrete HMM model pattern recognition techniques, potential heart beat data must be chosen (for example, with frame signal energy filtering) before performing pattern recognition. However, it can be difficult to select frames for processing which have potential heart beat data based on the frame energy if the received signal is noisy or the background noise has more energy than the heart beat portion of the signal within some time period of the frame. A pattern recognition technique that may be used without selecting potential heart beat data is a Viterbi algorithm search technique which uses a continuous HMM. The Viterbi search algorithm is used to find a most likely state sequence for a given observation sequence (extraction features) based on one or more heart beat HMM models and noise HMM models and a grammar network.

A grammar network defines the allowable state sequences semantically. A generated state sequence from the Viterbi search may not be a valid sequence without the constraints of the grammar network. In some embodiment, the grammar network is defined as below: [sil] {M1|M2|M3| ... } [sil], where 'M' represents a heart beat or a noise model and 'sil' represent a silent model. Once the state sequence is generated from an observation sequence of features derived from the frame signal data, a determination is made as to whether the extracted feature sequence is associated with a heart beat model or noise model.

Using traditional signal analysis techniques, it can be difficult to identify a heart beat or noise based only on amplitude, timing, frequency and other data taken from the signal when the subject is exercising. By comparing the features extracted from the signal reflected from a subject's artery to known patterns of different types of heart beats and noise, a more sophisticated process is used to determine whether the signal contains a heart beat or not by recognizing the pattern of a heart beat (or noise). The pattern recognition process is useful for detecting a heart beat when noise is present at a similar frequency as blood flow through an artery, such as while a subject is exercising.

The signal which is reflected from a target and processed by the present technology may be referred to herein as a "heartbeat" signal. This naming is used even though at the time of processing, it may not be confirmed that the signal (or frame or other portion of the signal being analyzed) represents a true heart beat. Rather, an analyzed portion of the signal is considered to potentially represent a heart beat until it is confirmed that the features associated with the signal represent a true heart beat. This is discussed in more detail below.

Noise may be generated within a signal reflected from the artery wall and/or the blood flow as a result of muscle or other movement of the subject during exercise, contact of the subject with a surface while running or other type or exercise, or from some other source. In some embodiments, with respect to the heart rate monitor discussed herein, noise can be considered any sound detected from a subject that is not associated with the subject's heart, blood flow, a heart beat or pulse.

The heart rate monitor of the present technology may extract several features from a frame of a signal reflected from a target. Examples of the features derived from the frame signal data include linear predictive coding (LPC) coefficients, cepstral coefficients, Mel Frequency Cepstral Coefficients (MFCC), perceptual linear prediction (PLP), formants, signal energy values, heart beat duration values, delta features (feature differences) and other features. In some embodiments, the present system may generate between eight to fourteen LPC coefficients for a frame of a received signal. In some embodiments, there may be 26 MFCC coefficients (including the log energy and delta) generated for a single frame of frame signal data. The cepstral coefficients may be generated from the LPC coefficients. The formant features may be estimated by finding the LPC roots. Heart beat duration and energy are determined from the signal itself and are discussed in more detail below.

In some embodiments, the heat beat and/or noise models are implemented as Hidden Markov models (HMM). Each model used to recognize a heart beat comprises one or more symbols. A symbol characterizes a basic pattern in a heart beat signal. In some embodiments, each symbol is an HMM model which contains a number of states, a number of distinct observation symbols per state, state transition probabilities and observation probability distribution. In some embodiments, a heart beat model may include a first symbol to reflect the main heart beat blood flow through an artery and a second symbol to reflect a back flow of blood through the artery immediately after increased blood flow due to the heart beat. Heart beat backflow is the temporary slowdown or reverse in blood flow that occurs in an artery after an increase in blood flow. When using two heart beat symbols, each symbol may have five states (excluding the start and end states), for a total of ten states for both symbols. Other numbers of states can be used for each symbol, and other numbers of symbols may be used in each heart beat model. A noise model may also have different numbers of symbols and states for each symbol.

There are several differences in processing a subject's heartbeat signal compared to a subject's speech signal. Important information for the ultrasound heartbeat signal is contained on a different frequency than that for speech signals. Typically, the ultrasound heartbeat signals have formants in lower frequencies than those of normal audio signals such as speech. In some embodiments, the formants which are estimated by processing the ultrasound signals may depend on the system used, including sensors, ADCs, filters and other system components. For example, ultrasound heartbeat signals can have formants in lower frequencies, such as 600-800 Hz and 1200-1600 Hz, while speech signals have formants in higher frequencies. Additionally, speech signals typically have three or more formants, rather than two formats as in the case of a heart beat. A formant is a peak of a resonant frequency for a signal. The formant range for a heartbeat signal may change according to a subject's gender, age, and activity. Typical speech recognition processes include a pre-emphasis function which boosts high frequency components and reduces low frequency components. This would result in reducing or eliminating the important Doppler shift frequency components.

Another difference in determining heartbeat signal features and speech features is the consideration of the signal duration. Typical speech recognition techniques may not use duration of a signal component because it is of little value. With heartbeat signal processing however, the duration of a heartbeat candidate can be used to eliminate false heart beats as noise or some other unwanted component or event. The duration of the blood flow due to a heart beat and the backflow of blood after the heart beat may be considered in heart beat models. For example, a set of HMM heart beat models may use two-symbol heart beat models, one symbol for the initial blood flow and one symbol for the back flow.

Embodiments of a heart rate monitor discussed herein may include a gel pad, an oil based transition medium, an adhesive member, power saving techniques and other features. In addition to the embodiments discussed below, these embodiments are described in the following patent and patent applications, all of which are hereby incorporated by reference in their entirety: U.S. Pat. No. 6,843,771, issued on Jan. 18, 2005, entitled "ULTRASONIC MONITOR FOR MEASURING HEART RATE AND BLOOD FLOW RATE," having inventors Thomas Ying-Ching Lo and Tolentino Escorcio; U.S. patent application Ser. No. 10/990,794, filed on Nov. 17, 2004, entitled "ULTRASONIC MONITOR FOR MEASURING BLOOD FLOW AND PULSE RATES", having inventor Thomas Ying-Ching Lo and Rong Jong Chang; U.S. patent application Ser. No. 10/991,115, filed on Nov. 17, 2004, entitled "GEL PAD FOR USE WITH AN ULTRASONIC MONITOR", having inventors Thomas Ying-Ching Lo and Rong Jong Chang; U.S. patent application Ser. No. 11/124,707, filed on May 9, 2005, entitled "AN ULTRASONIC MONITOR WITH A BIOCOMPATIBLE OIL BASED TRANSMISSION MEDIUM", having inventors Thomas Ying-Ching Lo and Rong Jong Chang; U.S. patent application Ser. No. 11/148,144, filed on Jun. 8, 2005, entitled "AN ULTRASONIC MONITOR WITH AN ADHESIVE MEMBER," having inventors Thomas Ying-Ching Lo and Rong Jong Chang; and U.S. patent application Ser. No. 11/402,476, filed on Apr. 2, 2006, entitled "POWER SAVING TECHNIQUES FOR CONTINUOUS HEART RATE MONITORING," having inventors Thomas Ying-Ching Lo and Karthik H. Katingari.

As discussed above, the technology discussed herein may be used with a variety of technologies. One suitable technology is ultrasound technology. The terms ultrasonic and ultrasound are used interchangeably herein and refer to a sound wave having a frequency between about 30 KHz and about 30 MHz. An ultrasonic transducer, or transducer element, as used herein is a device used to introduce sonic energy into and detect reflected signals from a living subject. Ultrasonic transducers respond to electric pulses from a driving device and ultrasonic pulses reflected by a subject.

FIG. 2A illustrates an embodiment of a wrist worn monitor system. The system of FIG. 2A includes a monitor module 210, a strap 220, a display device 230 and a transmission medium 240. Monitor module 210 detects blood flow through the radial artery at the subject's wrist. Heart rate data is then provided directly to display module 230. In one embodiment, connecting wires are molded into strap 220 between the monitor module 210 and display device 230.

The monitor can also be implemented with a remote display. The monitor system of FIG. 2B includes monitor module 260, first strap 270 attached to monitor module 260, remote display module 280 and second strap 290 attached to remote display module 280. Monitor module 260 detects the blood flow through a radial artery in the subject's wrist. Heart rate data is derived from the detected blood flow and provided to remote display module 280. Monitor 260 can wirelessly transmit information to remote display 280 using a wireless transmitter (not shown). The remote display 280 includes a receiver (not shown) to receive the transmission from monitor 260. The remote display 280 may be a monitor screen or other device.

The monitor of the present technology may be configured to suit a particular application. Examples of configurable monitor elements include signal frequency and transducer size. Determining what signal frequency to use may depend on the particular object being monitored and the technology being used. The wrist offers a convenient location for positioning the monitoring device. In some embodiments, the relatively shallow focal depth of the radial artery in the wrist is compatible with a high frequency carrier signal.

The size of the transducer or other transmitting elements also affects the signal frequency and the focal depth. With respect to ultrasound devices, thinner electromechanical resonators emit at higher frequencies. Transducer elements driven by high frequency signals tend to vibrate more rapidly and consume more power than those operating at lower frequencies. This is primarily due to internal loss. The monitor amplifier and demodulation circuits will also consume more power processing the higher frequencies.

Figure 3A:
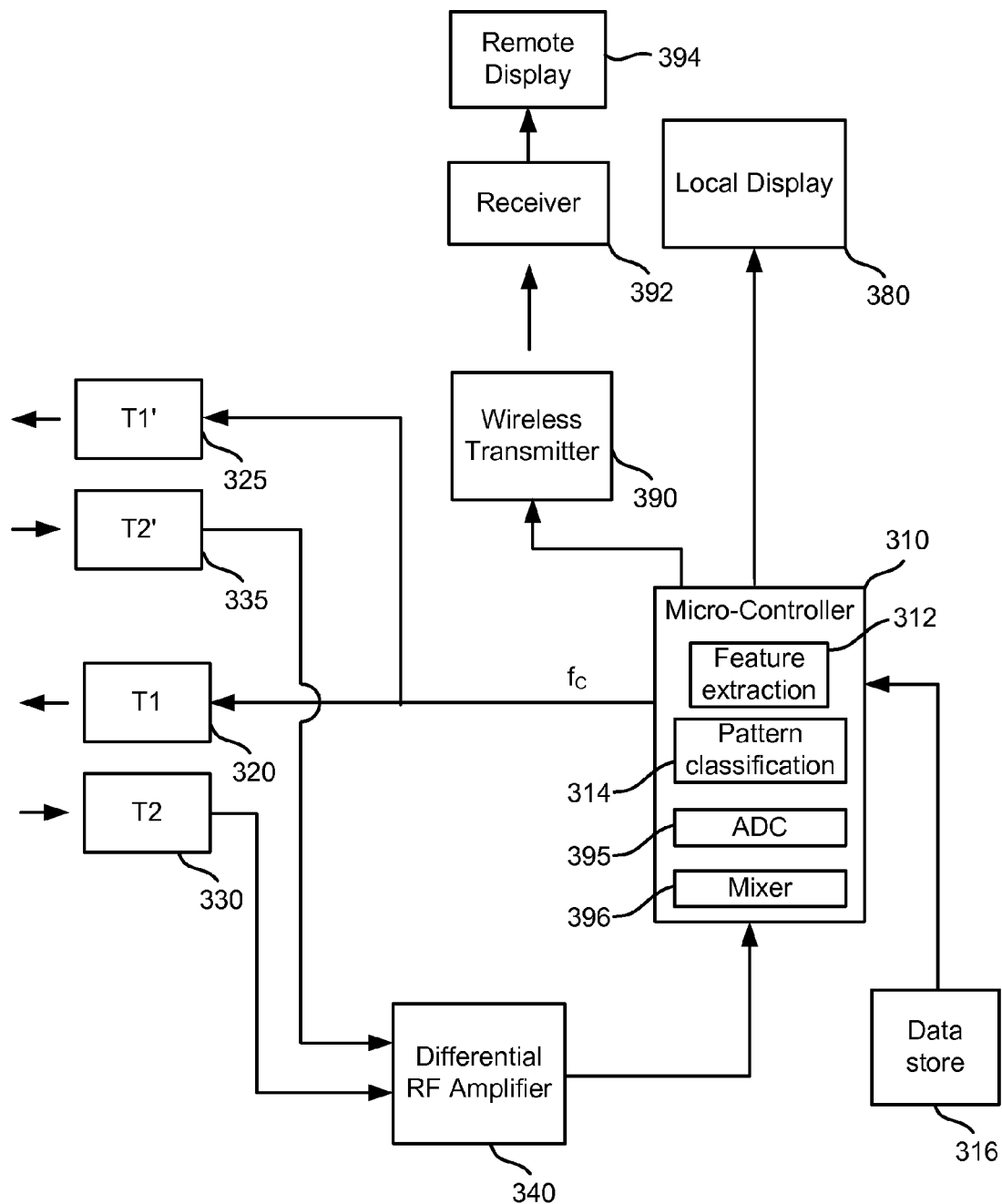
FIG. 3A is a block diagram of an embodiment of a system for determining a heart rate.

FIG. 3A is a block diagram of an embodiment of a system for determining a heart rate. The block diagram of FIG. 3A includes transducers 320, 325, 330 and 335, differential radio frequency (RF) amplifier 340, microcontroller 310, data store 316, local display 380, wireless transducer 390, receiver 392 and remote display 394. Operation of the system of FIG. 3A is discussed with respect to FIG. 4.

Any of several types of transducers may be used for transducers 320, 325, 330 and 335. One example is a K-350, Modified Lead Zirconate-Titanate transducer, by Keramos Division, Piezo Technologies. Equivalent materials to this type of transducer include PZT-5A or NAVY-II equivalent.

Figure 2B:
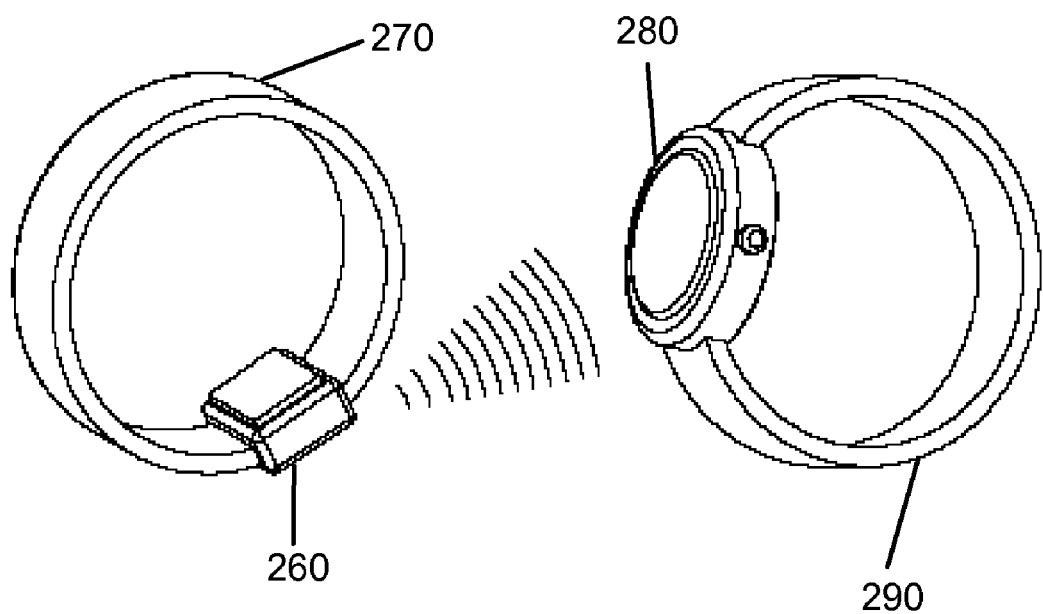
FIG. 2B is another example of a wrist worn heart rate monitor.
Figure 3B:
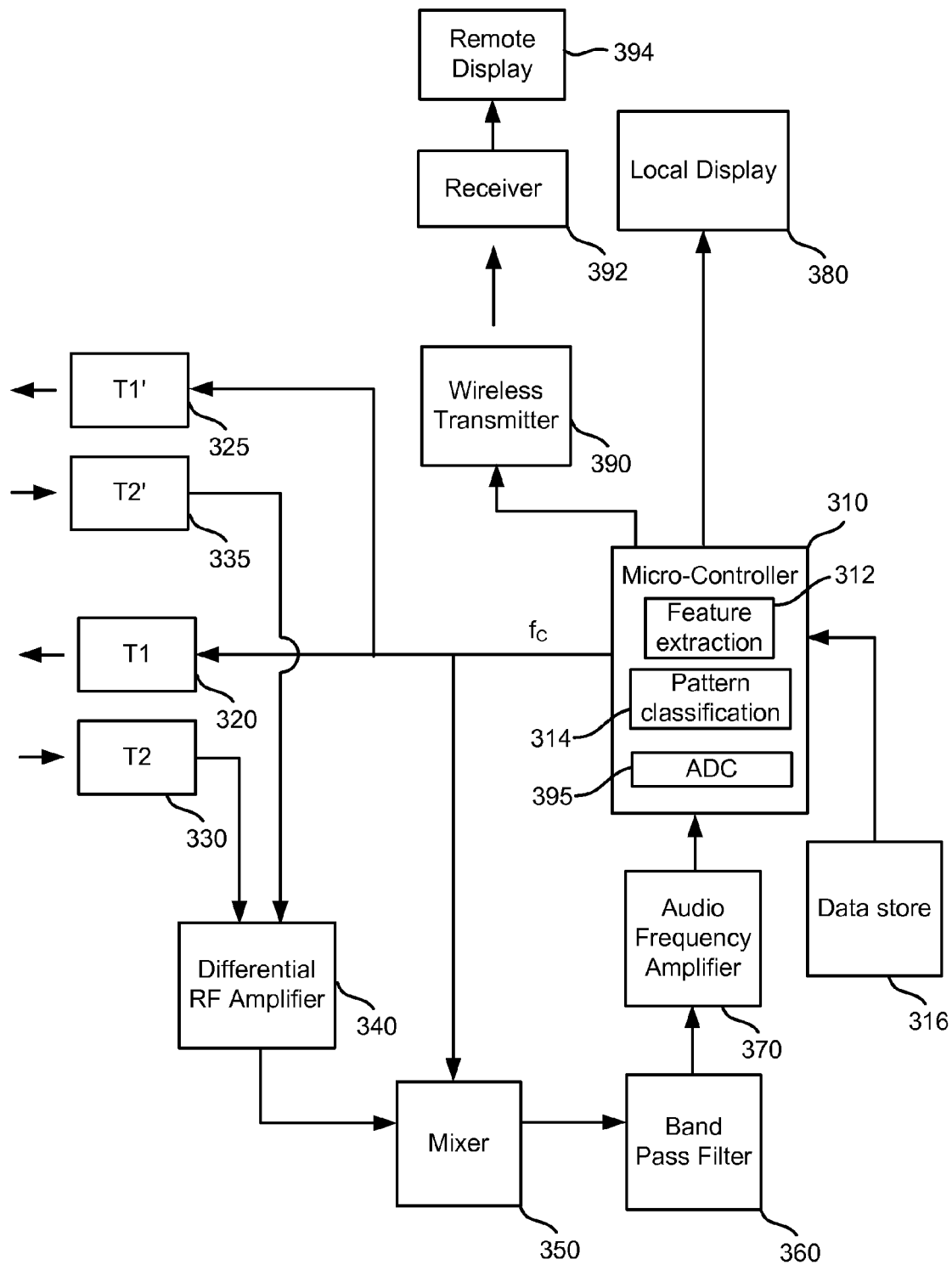
FIG. 3B is a block diagram of another embodiment of a system for determining a heart rate.
Figure 3C:
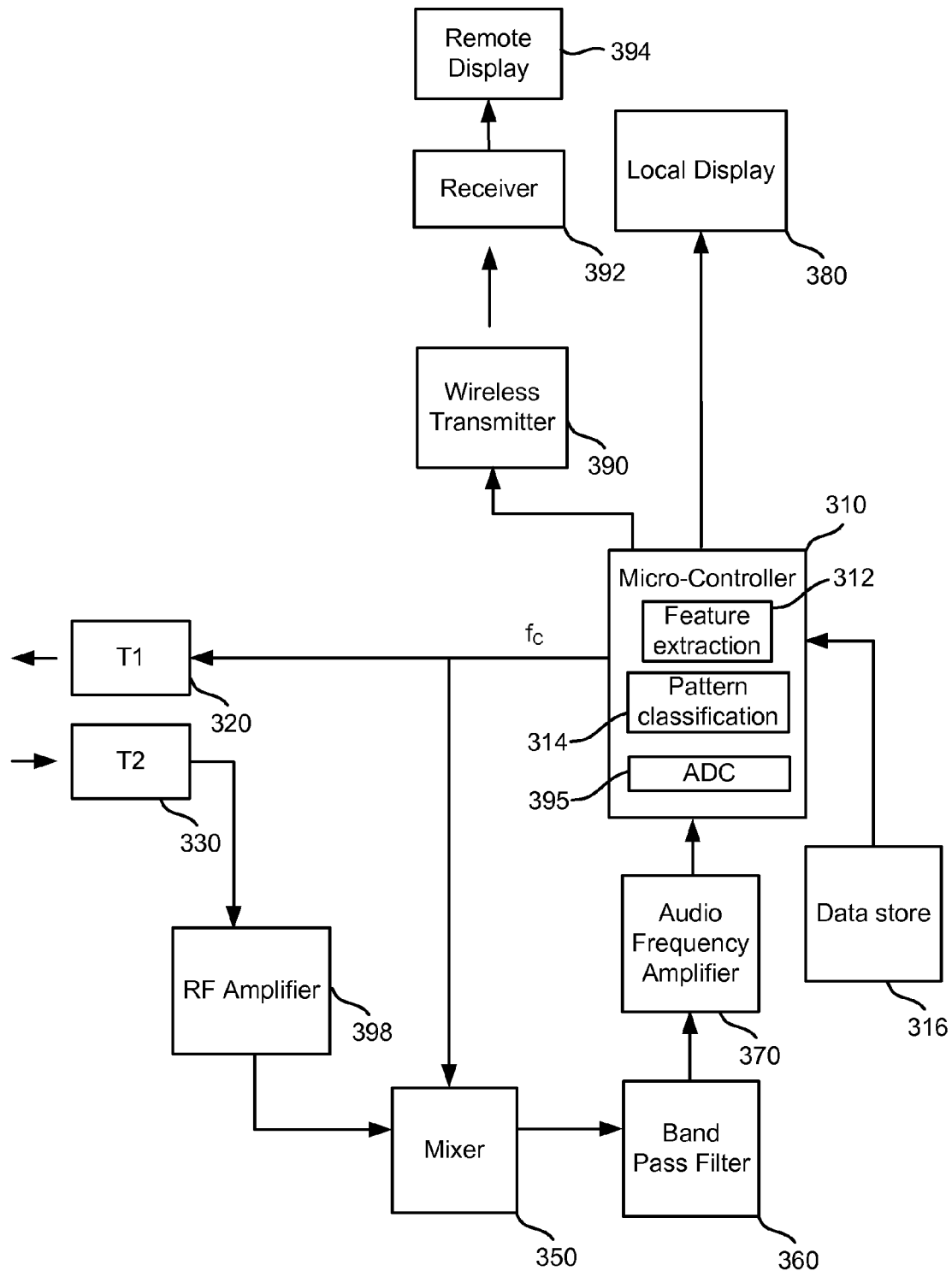
FIG. 3C is a block diagram of another embodiment of a system for determining a heart rate.

In some embodiments such as that illustrated in FIG. 2B, the signals which drive the transducers and the signals produced by the transducers are transmitted remotely to the other components of the heart rate monitor displayed in FIGS. 3A, 3B and 3C. The remote transmission of signals may be performed by transmitting devices not shown. In some embodiments, differential RF amplifier 340, micro-controller 310 and other devices are stored with the transducers on module 260 and processed data is sent from micro controller 310 to a display unit 280 using wireless transmitter 390 and receiver 392.

Differential RF amplifier 340 may receive signals from transducers 330 and 335 and amplify the signals. In some embodiments, the differential amplifier may amplify the difference of the signals received from transducers 330 and 335. For example, the signal provided by transducer 330 may include blood flow, blood vessel movement, noise due to muscle movement and other noise components. The signal provided by transducer 335 may include noise due to muscle movement and other noise components only (not blood flow or blood vessel component). The difference of the signals may be provided by differential RF amplifier 340 as the blood flow and blood vessel movement component only. Differential amplifier provides a single amplified signal to micro-controller 310.

Microcontroller 310 includes feature extraction module 312, pattern classification module 314, mixer 396 and analog to digital conversion (ADC) module 395. Microcontroller 310 of the monitor can be implemented as one or more of several common microcontroller integrated circuits, including Samsung S3C7335 series, Intel 8051 series, Texas Instruments MSP430 series microcontrollers and others, including a custom ASIC (application specific integrated circuit).

Mixer 396 within micro-controller 310 may be used to demodulate the analog difference signal received from differential RF amplifier 340. The demodulation may be performed with carrier frequency $f_c$ which is used to drive transmitting transducers 325 and 320. Mixer 396 may be implemented as software stored and executed within micro-controller 310 or as a built-in feature or mechanism of micro-controller 310.

ADC 395 may convert the demodulated signal from mixer 396 from analog format to digital format. ADC 395 may be implemented by a built-in ADC feature of micro-controller 310.

Feature extraction module 312 receives a processed reflected signal and extracts or derives a set of features (collectively called "extracted features") for each frame or frames of the reflected signal. The processed signal may be the signal received by transducers 330 and/or 335 after it has been amplified, demodulated, digitized and optionally otherwise processed. The extraction may involve LPC analysis, cepstral analysis, determining the frame signal energy and/or some other signal analysis. Feature extraction is discussed in more detail below.

Pattern classification module 314 processes the features extracted by feature extraction module 312 with respect to one or more feature templates, models, algorithms and other processing and determines whether the extracted feature sequence is associated with heart beats or noise. In some embodiments, the models are HMM models and the algorithms may include a Viterbi algorithm. Performing pattern classification for a set of heart beat features is discussed in more detail below.

Data store 316 may be any memory or storage device able to store one or more heart beat models, noise models, heart beat feature sets, noise feature sets, and other data. In some embodiments, data store 316 may be implemented using ROM, EERPOM, FLASH, or some other device or storage technology. Data store 316 may be located external to micro-controller 310 or within micro-controller 310.

Micro-controller 310 may identify heart beats, determine a subject's heart rate, and transmit heart rate information and other data to local display 380 or wireless transmitter 390. Local display 380 may display the heart rate information and related data through an LCD or some other display mechanism. Wireless transmitter 390 may transmit the heart rate information to receiver 392. Receiver 392 may receive the heart rate information and transmit the data to remote display 394, which may display the heart rate information and related data through an LCD or some other display mechanism.

FIG. 3B is a block diagram of another embodiment of a system for determining a heart rate. The block diagram of FIG. 3B includes transducers 320, 325, 330 and 335, differential RF amplifier 340, mixer 350, band pass filter 360, audio frequency amplifier 370, microcontroller 310, data store 316, local display 380, wireless transducer 390, receiver 392 and remote display 394.

The system of FIG. 3B is similar to that of FIG. 3A except for the addition of mixer 350, band pass filter 360, audio frequency amplifier 370. Mixer 350 of the monitor replaces mixer 396 implemented within the micro-controller of FIG. 3A and is used to demodulate the analog difference signal received from differential RF amplifier 340. The demodulation may be performed with carrier frequency $f_c$ which is provided by micro-controller 310 and used to drive transmitting transducers 325 and 320. Mixer 350 can be implemented as one or more of several common mixer ICs or frequency demodulation ICs. A non-exclusive list of possible mixer ICs include NJC's NJM2295, NJM2292 and NJM2537 mixers, Toko's TK83361M mixer, Motorola's MC3371 mixer and a custom ASIC (application specific integrated circuit).

Band pass filter 360 may allow frequency bands to pass from mixer 350 to amplifier 370. The pass band may be set according to the particular system design. In some embodiments, the band pass filter may have a pass band of 500 Hz to 2000 Hz. Thus, the filter may prevent noise having a frequency below 500 Hz from passing to amplifier 370, as well as to prevent aliasing in the signal depending on the data sampling rate in microcontroller 310.

Audio frequency amplifier 370 may amplify the filtered signal. The signal may be amplified for easier processing by micro-controller 310. In some embodiments, audio frequency amplifier 370 may be implemented within micro-controller 310.

FIG. 3C is a block diagram of another embodiment of a system for determining a heart rate. The block diagram of FIG. 3C includes transducers 320 and 330, RF amplifier 398, mixer 350, band pass filter 360, audio frequency amplifier 370, microcontroller 310, data store 316, local display 380, wireless transducer 390, receiver 392 and remote display 394. The block diagram of FIG. 3C is similar to that of FIG. 3B except that only one pair of transducers is used. Thus, transducer 320 is driven by a carrier frequency signal $f_c$ provided by micro-controller 310. Transducer 330 receives a signal reflected from a subject and provides the reflected signal to RF amplifier 398.

Figure 3D:
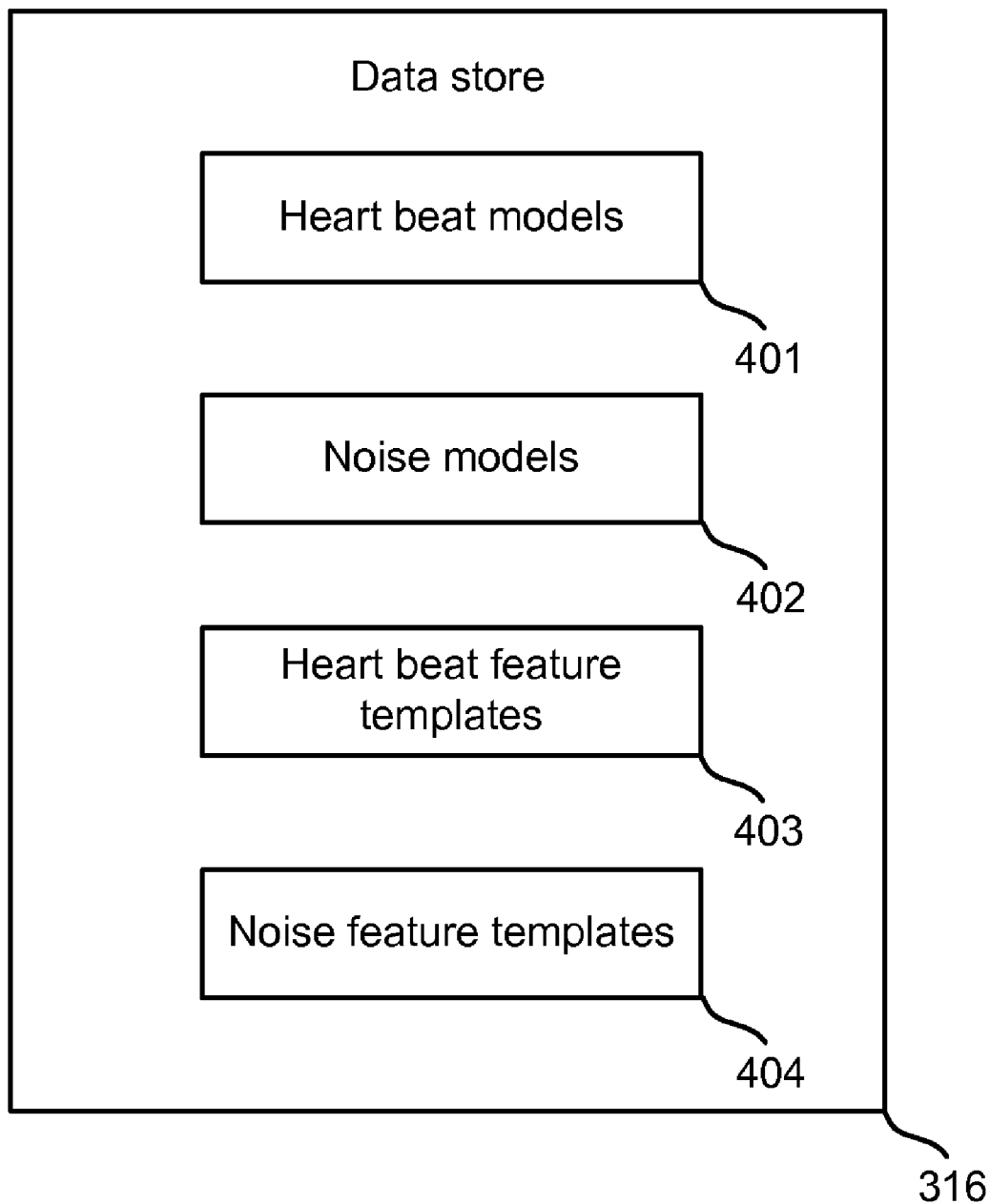
FIG. 3D is a block diagram of an embodiment of a data store.

FIG. 3D is a block diagram of an embodiment of a data store 316. Data store 316 includes heart beat models 401, noise models 402, heart beat feature templates 403, and noise feature templates 404. Each feature template may include a set of features extracted from frame signal data from a known heart beat, noise or some other type of data. The models and template feature sets may be accessed by micro-controller 310 to determine whether a signal includes a heart beat. Data store 316 may include additional data as well, such as one or more modules or instructions for implementing one or more algorithms for pattern classification, such as a Viterbi algorithm.

Figure 4:
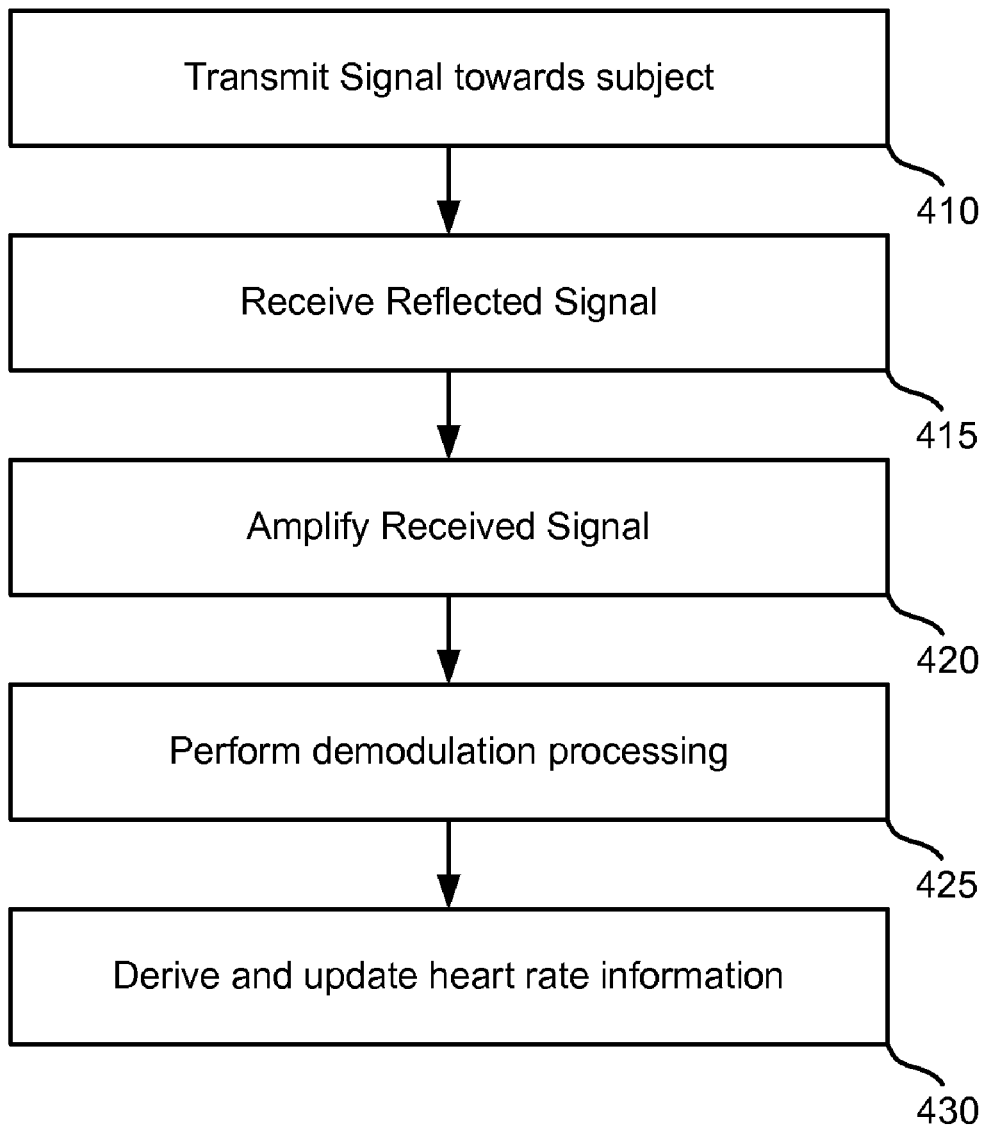
FIG. 4 is a flowchart of an embodiment of a method for determining a heart rate.

FIG. 4 is a flow chart of an embodiment of a process for operation of a heart rate monitor, such as the monitors of FIGS. 3A, 3B and 3C. First, a signal is transmitted towards a subject at step 410. With respect to the system of FIGS. 3A-C, microcontroller 310 drives transmitting transducer element 320 with a carrier signal $f_C$. In some embodiments, microcontroller drives transducers 320 and 325. The transmitting transducer transmits or generates a signal in response to the driving signal. In one embodiment, with respect to ultrasound monitors, the carrier signal may be within a range of 30 KHz to 30 MHz. In another embodiment, the carrier signal may be within a range of 1 MHz to 10 MHz. In yet another embodiment, the carrier signal is about 5 MHz. In some embodiments, the carrier signal may have a frequency in other ranges.

A reflected signal is received at step 415. The reflected signal is generated when the transmitted signal of step 410 reflects from a blood vessel of a subject. When the monitor is worn on a wrist, the radial artery reflects the transmitted signal. The received signal will contain a carrier frequency that has experienced a Doppler shift from the signal transmitted by transmitting transducer 320. The reflected signal may contain a Doppler Shift based on artery blood flow and artery expansion due to the blood flow. The reflected signal may also contain noise due to muscle movement by the subject, for example due to exercise such as running or some other exertion.

After receiving the reflected signal, the received signal is amplified at step 420. The received signal is amplified by a factor that allows the signal to be processed further. In some embodiments, the received signal is amplified by a factor that allows the signal to be processed for demodulation by the system of FIG. 3A-C. With respect to FIGS. 3A and 3B, differential RF amplifier 340 is used to amplify the difference between the reflected signal received by transducers 330 and 335. The amplified signal is then output by the amplifier. In a monitor with one pair of receiving and transmitting transducers such as that in FIG. 3C, RF amplifier 398 is used to amplify the output of the receiving transducer.

After amplifying, demodulation processing may be performed on the signal at step 425. The demodulation processing may demodulate the signal and prepare the resulting signal for processing. Demodulation may be performed by a demodulation and/or mixer IC, such as mixer 350 of FIGS. 3B and 3C, or software or some other mechanism of microcontroller 310 of FIG. 3A. Demodulation processing may also include converting the demodulated analog signal to digital format. Demodulation processing of a signal is discussed in more detail below with respect to FIG. 5.

Heart rate information is derived and updated from the signal at step 430. Deriving the heart rate may include recognizing heart beats in the signal. Recognizing a heartbeat may include determining features of a frame in the reflected signal and performing pattern classification on the extracted features. Deriving a heart rate by recognizing heart beats is discussed in more detail below with respect to the method of FIG. 6.

Figure 5:
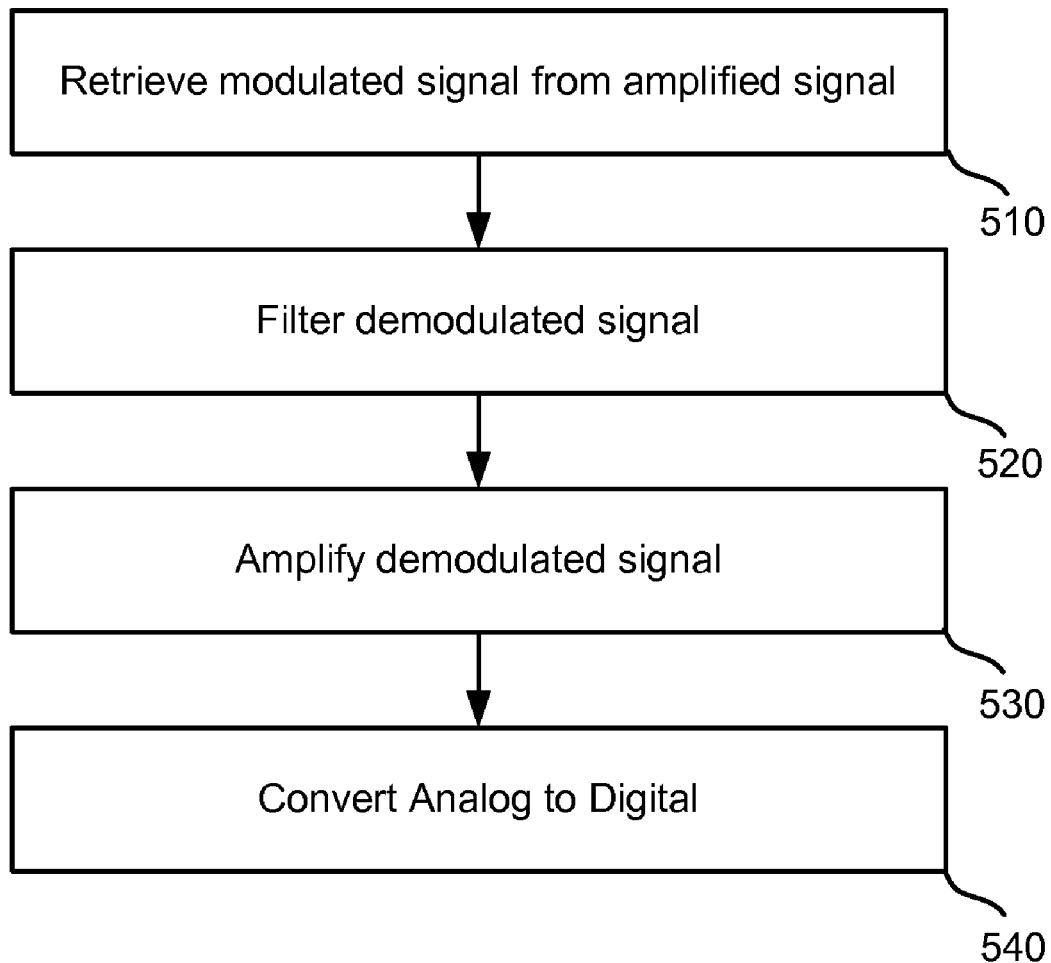
FIG. 5 is a flow chart of an embodiment of a method for performing demodulation processing.

FIG. 5 illustrates a flow chart of an embodiment of a method for performing demodulation on a signal. The demodulation process may be implemented by mixer 350, amplifier 360 and filter 370 of FIGS. 3B-3C or at least partially by micro-controller 310. In some embodiments, the method of FIG. 5 provides more detail for step 425 of the method of FIG. 4. First, a modulated signal is retrieved from an amplified signal at step 510. In some embodiments, the amplified signal provided by amplifier 340 or 398 is processed by a mixer to retrieve the modulated signal. The mixer uses the carrier signal $f_C$ to demodulate the reflected signal in order to extract the Doppler signal. Accordingly, the mixer is driven by carrier signal $f_C$ and the reflected signal. The mixer may be implemented as mixer 350 of FIGS. 3B and 3C or mixer 396 of FIG. 3A.

The demodulated signal is filtered at step 520. In one embodiment, the filter used in step 520 is band pass filter 360. The demodulated signal may be filtered by band pass filter 360 or by software or some other mechanism of micro-controller 310. Band pass filter 360 may be configured to remove aliasing effects, noise, and other unwanted frequency elements. In some embodiments, the band pass filter may be implemented with a high pass and low pass filter. In some embodiments, filtering of the demodulated signal may be implemented within micro-controller 310.

The filtered signal is then amplified at step 530. In some embodiments, the output of mixer 350 will have a frequency component in the audio range. The output may be amplified by audio frequency amplifier 370 or by software or some other mechanism of micro-controller 310. Amplifier 370 is an audio amplifier designed to amplify the demodulated audio range Doppler frequencies. For mixer output signals having non-audio range frequencies, other circuitry may be used to process the signal.

The demodulated signal of step 530 is then processed by an analog to digital converter at step 540. In one embodiment, the digitization is performed if it was not performed earlier. For example, the demodulated signal may be converted to digital format by ADC 395 of FIGS. 3B and 3C.

Figure 6:
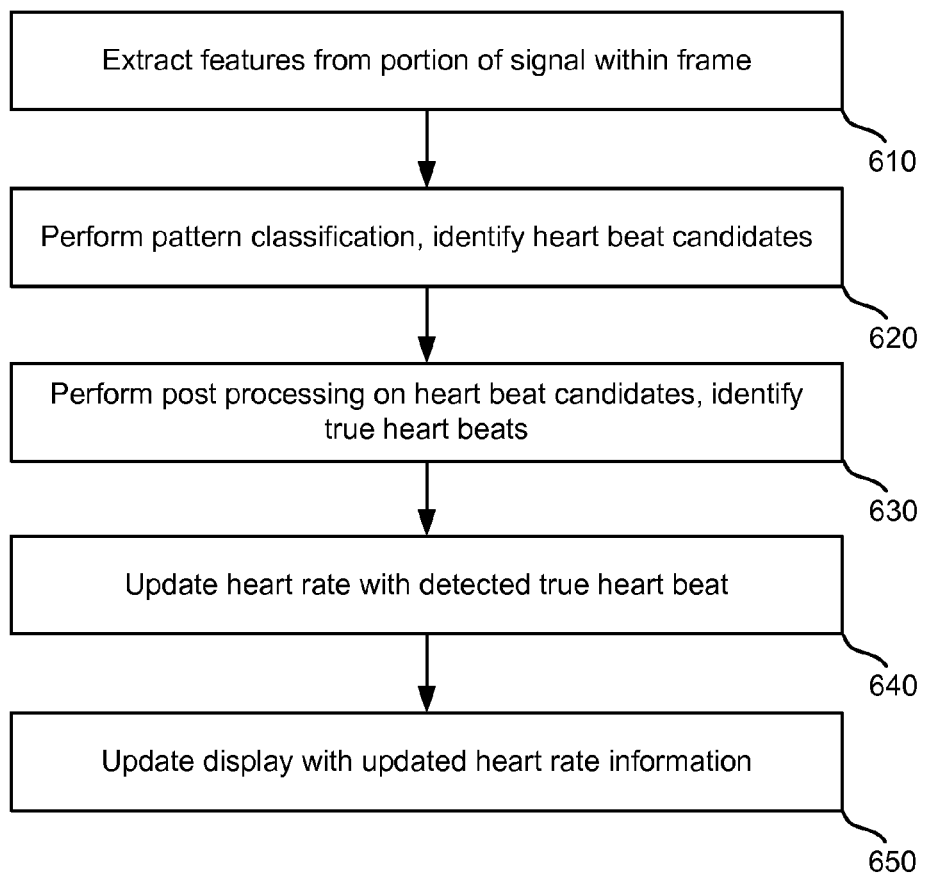
FIG. 6 is a flowchart of an embodiment of a method for deriving heart rate information by recognizing a heart beat signal.

FIG. 6 is a flowchart of an embodiment of a method for recognizing heart rate information. The method of FIG. 6 provides more information for step 430 of the method of FIG. 4 and may be implemented, for example, by any of the systems of FIGS. 3A-3C.

First, features are extracted from a portion of the signal within a frame at step 610. Extracting the features may include dividing the signal into frames and performing feature extraction analysis on each frame by feature extraction module 312. In one embodiment, the features may be extracted using LPC analysis, cepstral analysis and/or other methods. Extracting features is discussed in more detail below with respect to FIG. 7.

Pattern classification is performed and heart beat candidates are identified at step 615. Pattern classification may be performed in any of several ways, for example by template comparison for sets of extracted features, discrete HMM model techniques, Viterbi search algorithm and continuous HMM model techniques, and other methods. In some embodiments, more than one pattern classification method may be used to process extraction features. For example, if a feature template technique did not provide reliable results, a discrete HMM model techniques or Viterbi search algorithm technique may be used as well. In some embodiments, multiple techniques are used and the final result is determined from a 'vote' associated with each technique as to whether the signal data contains a heart beat on not. In some embodiments when using more than one technique, one or more of the techniques may be weighted based on past results, frame signal characteristics, and/or user input. In any case, if the extracted features are determined to be associated with a template or model associated with a heart beat, the frame signal data is considered a heart beat candidate. Performing pattern classification is discussed in more detail below with respect to FIG. 9 for feature templates, with respect to FIG. 10 for discrete HMM models, and with respect to FIG. 11 for Viterbi algorithm techniques.

Post-processing may be performed on heart beat candidates at step 630. The post-processing may include comparing the heartbeat candidate timing to an acceptable range of potential heartbeat thresholds. For example, if a heartbeat candidate is within a range of acceptable heart beat times, the heartbeat may be accepted as a true heartbeat. If the current heartbeat candidate is outside the acceptable range, then the heartbeat candidate can be dismissed as a false heartbeat. Post-processing of a heart beat candidate is discussed in more detail below with respect to FIG. 14.

After post-processing is performed, any identified true heart beat is used to update the heart rate at step 640. In this case, the time between the previous heartbeat and the newly detected heartbeat is determined as the heart rate period. The heart rate itself is determined as the inverse of the period. After the heart rate is detected, a display is updated with new heart rate information provided through the display at step 650. In some embodiments, updating a display may include providing a change display signal or some other data to local display 380 or remote display 394 through wireless transducer 390 and receiver 392. The data may include the new value of the heart rate, an amount to change a heart rate by, or some other information used to update the heart rate display.

Figure 7:
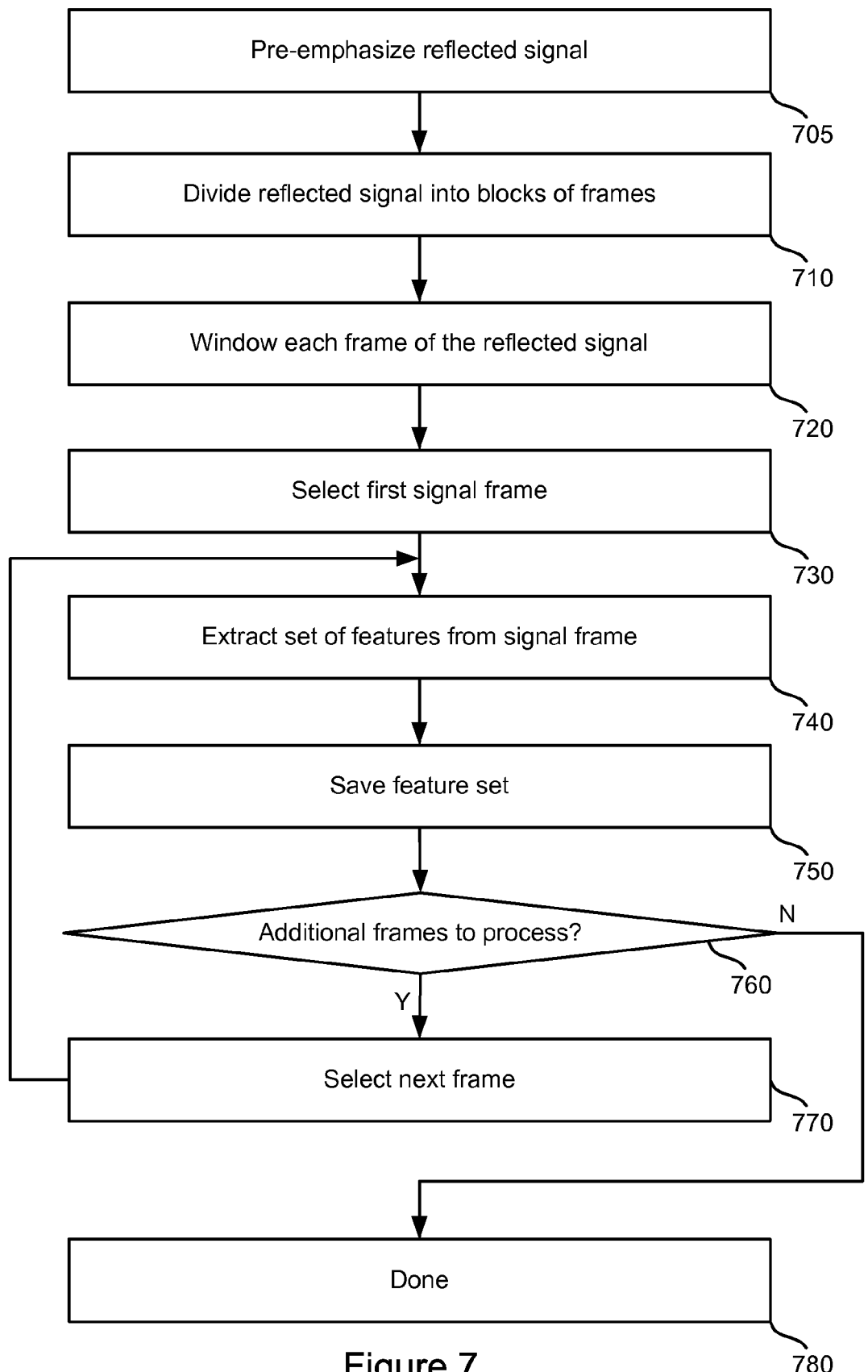
FIG. 7 is a flowchart of an embodiment of a method for extracting heartbeat features.

FIG. 7 is a flowchart of an embodiment of a method for extracting heartbeat features from a signal. In some embodiments, the method of FIG. 7 is implemented by feature extraction module 312 and provides more detail for step 610 of the process of FIG. 6. First, the reflected signal transmitted to micro-controller 310 is pre-emphasized at step 705. Pre-emphasis of the reflected signal may include filtering the signal to boost the high frequency and remove the offset of the signal. The filter may be any of several filters used for this purpose, including a first order FIR filter described by the function below:

$$H(z)=1-az^{-1},$$

wherein a is a constant having a value between 0.9 and 0.99. In some embodiments, the value of the constant a is selected such that the resonant frequencies of the ultrasound signal in ranges of 600-800 Hz and 1200-1600 Hz are not reduced. These frequency values correspond to formant values which may be used as part of an observation sequence for the reflected signal. For example, the value of a may be 0.975. Applying a filter to the signal to pre-emphasize the signal may also result in removing or reducing the DC component of the heartbeat signal.

Next, the reflected signal is divided into blocks of frames at step 710. In some embodiments, the reflected signal received by transducer 330 may comprise a single continuous signal. To process this signal, the continuous reflected signal is divided into blocks of one or more frames. The blocks may be continuous or be separated by some time period. The signal may be divided into frames as the signal is received by feature extraction module 312. For example, each block may have a time period of 30-45 milliseconds. In some embodiments, the time period may be defined in terms of the sampling frequency of the signal. For example, frames may be described by the function:

$$x_l(n)=\tilde{S}(Ml+n),$$

where the reflected signal is divided into frames of N samples, with adjacent frames being separated by M samples, n has a value between 0-(N−1) and 1 has a value between 0-(L−1), L being the number of frames. In some embodiments, each frame may overlap one or more neighboring frames. For example, a frame that is 45 milliseconds in length may overlap a previous frame by 30 milliseconds. The signal data within a particular frame of a signal is herein referred to as frame signal data.

Each frame of the reflected signal is windowed within the frame at step 720. In some embodiments, any of several window shaping functions may be used to reshape the reflected signal within the selected frame. Reshaping the frame signal may include minimizing the signal discontinuities within the borders of each frame. In some embodiments, windowing a frame signal by reshaping includes spectrally flattening the signal. Reshaping a frame may be performed according to the function:

$$\tilde{x}_l(n)=x_l(n)w(n),$$

for n having values from 0 to (N−1), where the window function w(n) (Hamming Window) may be defined as:

$$w(n) = 0.53836 - 0.46164\cos\left(\frac{2\pi n}{N-1}\right).$$

After reshaping the signal window in the selected frame, the first signal frame is selected at step 730. Next, a set of features are extracted from the signal frame within at step 740. The features may be extracted using one or more techniques. For example, the features may be extracted using a combination of LPC analysis and cepstral analysis techniques. Other techniques and coefficients may be used as well, such as perceptual linear prediction (PLP) and Mel-frequency cepstrum coefficients (MFCC). In some embodiments, use of PLP and MFCC may result in coefficients that are more noise robust, depending on the particular heart rate monitor design. Extracting a set of features from a frame is discussed in more detail below with respect to FIG. 8. The extracted feature set is then saved at step 750. The feature set may be saved within micro-controller 310, to data store 316 or some other storage location.

A determination is then made as to whether more frames exist to be processed at step 760. In some embodiments, all the frames of the reflected signal can be processed. In some embodiments, calculations are performed for one or more frames consecutively during the method of FIG. 7. In some embodiments, by analyzing several overlapping frames at once, a determination may eventually be made if a frame signal represents a heartbeat candidate. If additional frames need to be processed, the next frame is selected at step 770 and the flowchart returns to step 740. If no additional frames exist to be processed, then the process of FIG. 7 is done at step 780. In some embodiments, the pattern classification module 314 will be notified that the feature sets of the reflected signal are available when the method of FIG. 7 ends at step 780.

Figure 8:
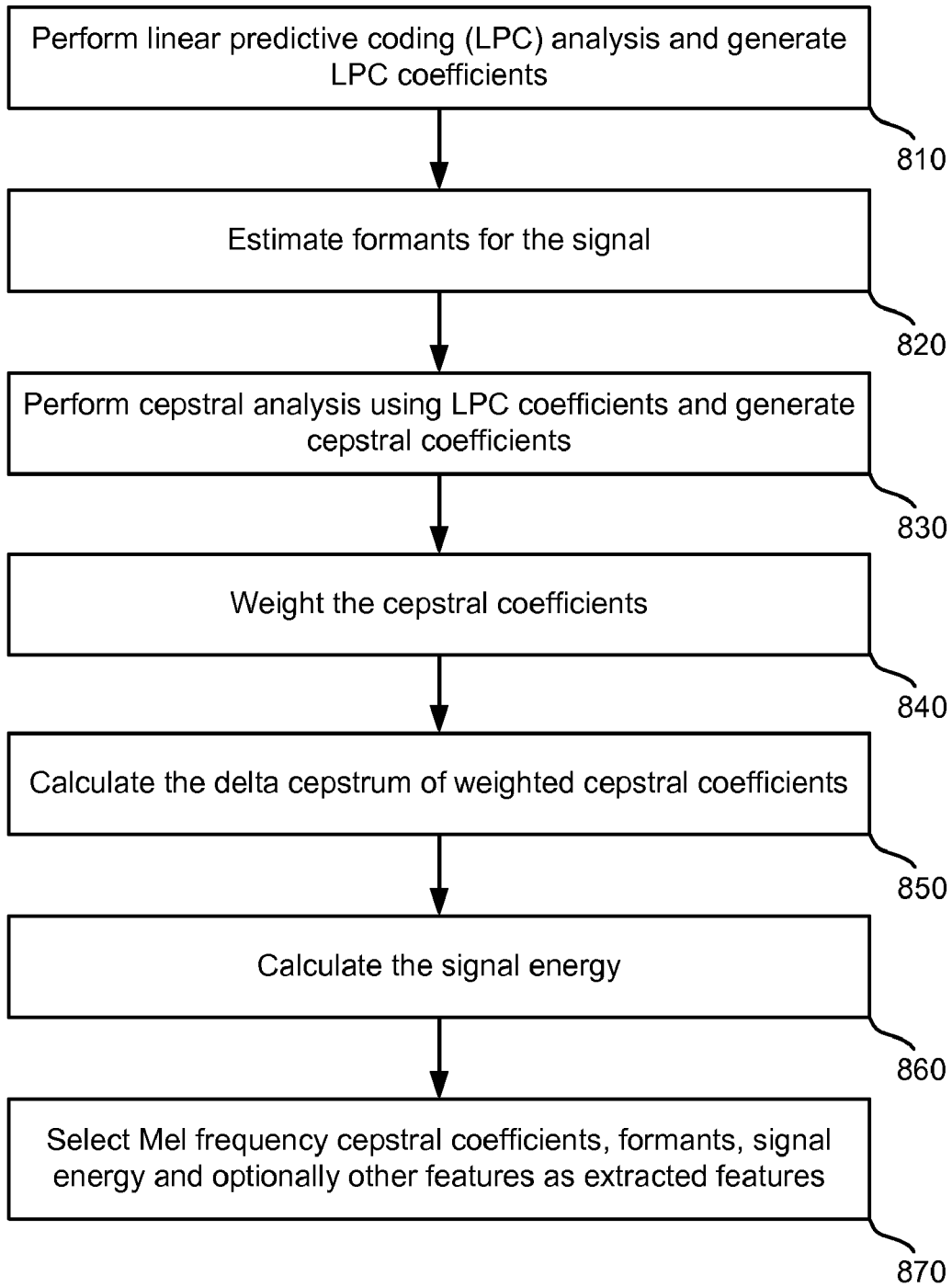
FIG. 8 is a flowchart of an embodiment of a method for extracting a set of features from signal frames.

FIG. 8 is a flowchart of an embodiment of a method for extracting a set of features from a frame signal. In some embodiments, the flowchart of FIG. 8 provides more detail for step 740 of the method of FIG. 7. The embodiment discussed with respect to FIG. 8 utilizes linear predictive coding and cepstral analysis. However, it is intended and should be understood that other methods may be used to generate a set of features for a frame signal as well.

First, linear predictive coding (LPC) analysis is performed and LPC coefficients are generated at step 810. The LPC coefficients are generated as a result of the LPC analysis. In some embodiments, the LPC analysis may use an autocorrelation method of an order p, where the number of coefficients generated is p+1. In matrix form, Ra=r, where the correlation vector is defined by the function:

$$r = [r(1) r(2) \ldots r(3)]^T,$$

the filter coefficients vector is:

$$a = [a_1 a_2 \ldots a_p]^T,$$

and the autocorrelation vector is:

$$R = \begin{bmatrix} r(0) & r(1) & r(2) & \cdots & r(p-1) \\ r(1) & r(0) & r(1) & \cdots & r(p-2) \\ r(2) & r(1) & r(0) & \cdots & r(p-3) \\ \vdots & \vdots & \vdots & \vdots & \vdots \\ r(p-1) & r(p-2) & r(p-3) & \cdots & r(0) \end{bmatrix}.$$

The matrix provides a solution of:

$a = R^{-1} r$. In some embodiments, the matrix may contain 8-14 LPC coefficients.

Formants are estimated for the signal at step 820. In some embodiments, a formant may be a peak in an acoustic frequency spectrum which results from the resonant frequencies of an acoustical system. A formant may be estimated by identifying peaks in resonant frequencies of the heartbeat signal or by finding the LPC roots. In some embodiments, determining formants is optional.

Formants for a frame signal associated with a potential heart beat will typically exist in ranges between 600-800 Hz and 1200-1600 Hz. Thus, a frame signal that contains a heart beat will have formants in these two ranges. Unlike a heart beat, human speech typically has three or more formants in different ranges. Thus, estimating the formants for a heart beat is different than determining formants for human speech.

Cepstral analysis is performed based on LPC coefficients at step 830. Performing cepstral analysis may include generating cepstral coefficients from the LPC coefficients generated at step 810. Cepstral coefficients may include coefficients of the Fourier transform representation of the log magnitude of the heartbeat signal spectrum. In some embodiments, other types of cepstral coefficients may be generated, such as Mel Frequency cepstral coefficients.

In some embodiments, the cepstral coefficients may be derived from a set of LPC coefficients $a_i$, for i=1–p, using the recursion function:

$$c_o = r(0),$$

$$c_m = a_m + \sum_{k=1}^{m-1} \frac{k}{m} c_k a_m - k,$$

where m is a value between 1–p, and $$c_m = \sum_{k=m-p}^{m-1} \frac{k}{m} c_k a_m - k,$$

where m is greater than p (m>p). In some embodiments, m may be the number of coefficients, for example 12 or 14.

After the cepstral analysis, the cepstral coefficients may be weighted at step 840. The weighting may be performed for some cepstral coefficients which should be weighted more or considered more important than other cepstral coefficients. Selecting more important cepstral coefficients to weight may be done based on the particular system requirements, the subject being monitored, the particular monitor hardware and software, or other factors. The weighting may be implemented on the cepstral vector cm by a weighting function, such that:

$$\hat{c}_l m = c_l(m) W_c(m),$$

wherein the weighting function is described as:

$$W_c(m) = 1 + \frac{Q}{2} \sin\left(\frac{\pi m}{Q}\right),$$

where m has a value between 1 and Q, inclusive, wherein Q is the number of coefficients of the cepstral vector.

After weighting the cepstral coefficients, the delta cepstrum is determined at step 850. The delta cepstrum is the difference between a set of cepstral coefficients for one frame signal with cepstral coefficients of a previous frame signal. Determining the delta cepstrum of the weighted cepstral vector sequence can be determined as:

$$\Delta \hat{c}_l m = \left[ \sum_{k=-K}^{K} k \hat{c}_{l-k}(m) \right] G,$$

where m has a value between 1 and Q, and G is a gain which is chosen to set $\hat{c}_l(m)$ and $\Delta \hat{c}_l(m)$ equal or approximately the same value.

After the delta cepstrum (cepstrum coefficient differences) is determined, the frame signal energy is calculated at step 860. The frame signal energy may be determined in several ways, such as by taking the log value of the squared energy value, or $e = \log(S^2)$. In some embodiments, the frame signal energy is used to compare differences or the distortion between the frame energy of a reflected signal and a feature template.

A set of extracted features is selected and stored at step 870. The set of extracted features for the frame signal data may include Mel Frequency cepstral coefficients, formants, signal energy and optionally other data. For example, the extracted set of features may include the weighted cepstral vector and the corresponding weighted delta or difference cepstrum vector. The features may be concatenated together, where the concatenation may be expressed by the function:

$$Q_l = \{\hat{c}_l(m), \Delta \hat{c}_l(m)\},$$

and may consist of a finite number of coefficients per vector, such as 24. In some embodiments, the value of the energy is set as a value for one of the $Q_l$ function values for each heartbeat. In some embodiments, cepstrum mean subtraction may be applied to the cepstral coefficients to derive at least a portion of the observation features.

Figure 9:
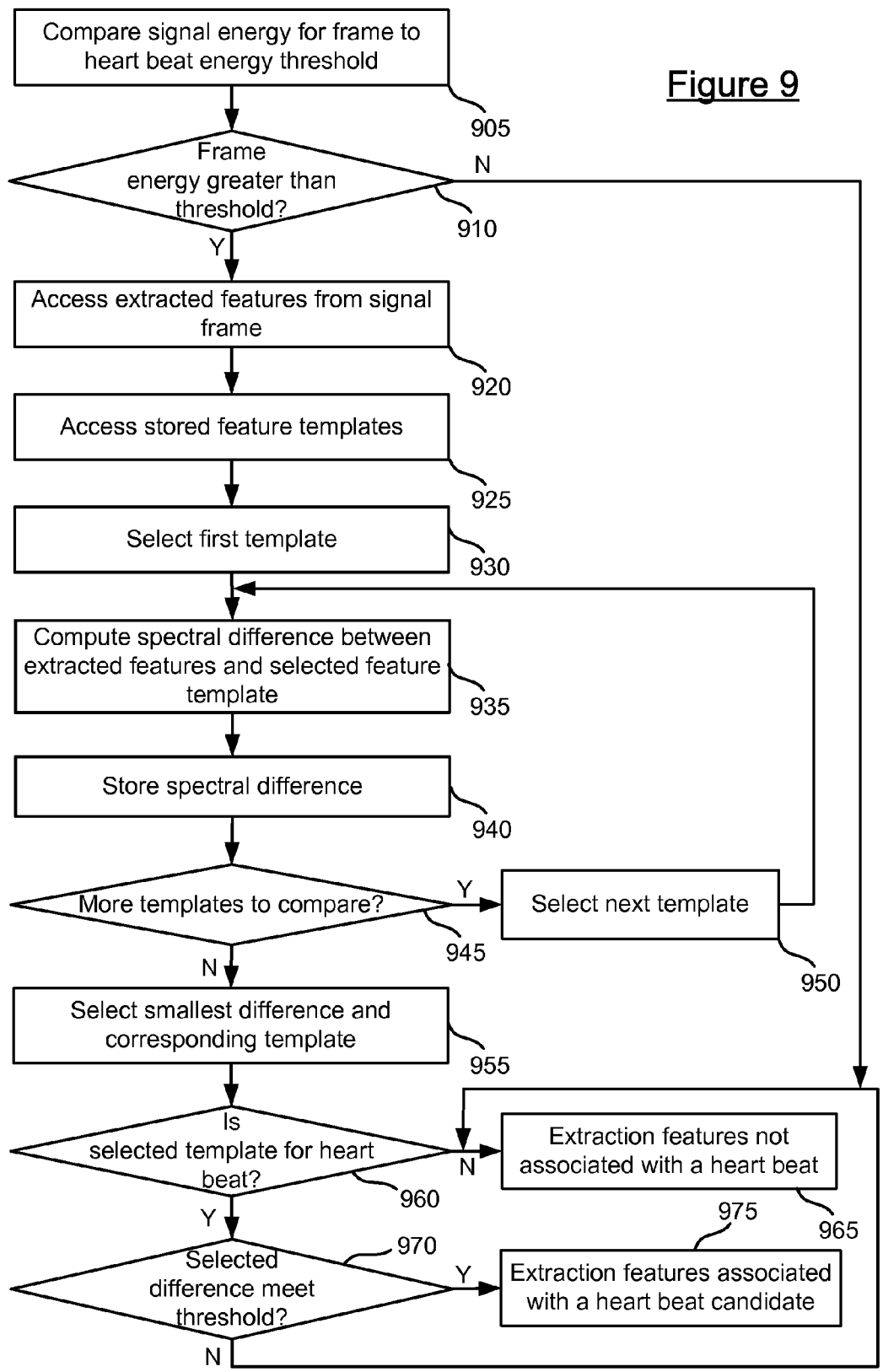
FIG. 9 is a flowchart of an embodiment of a method for performing pattern classification using feature templates.
Figure 10:
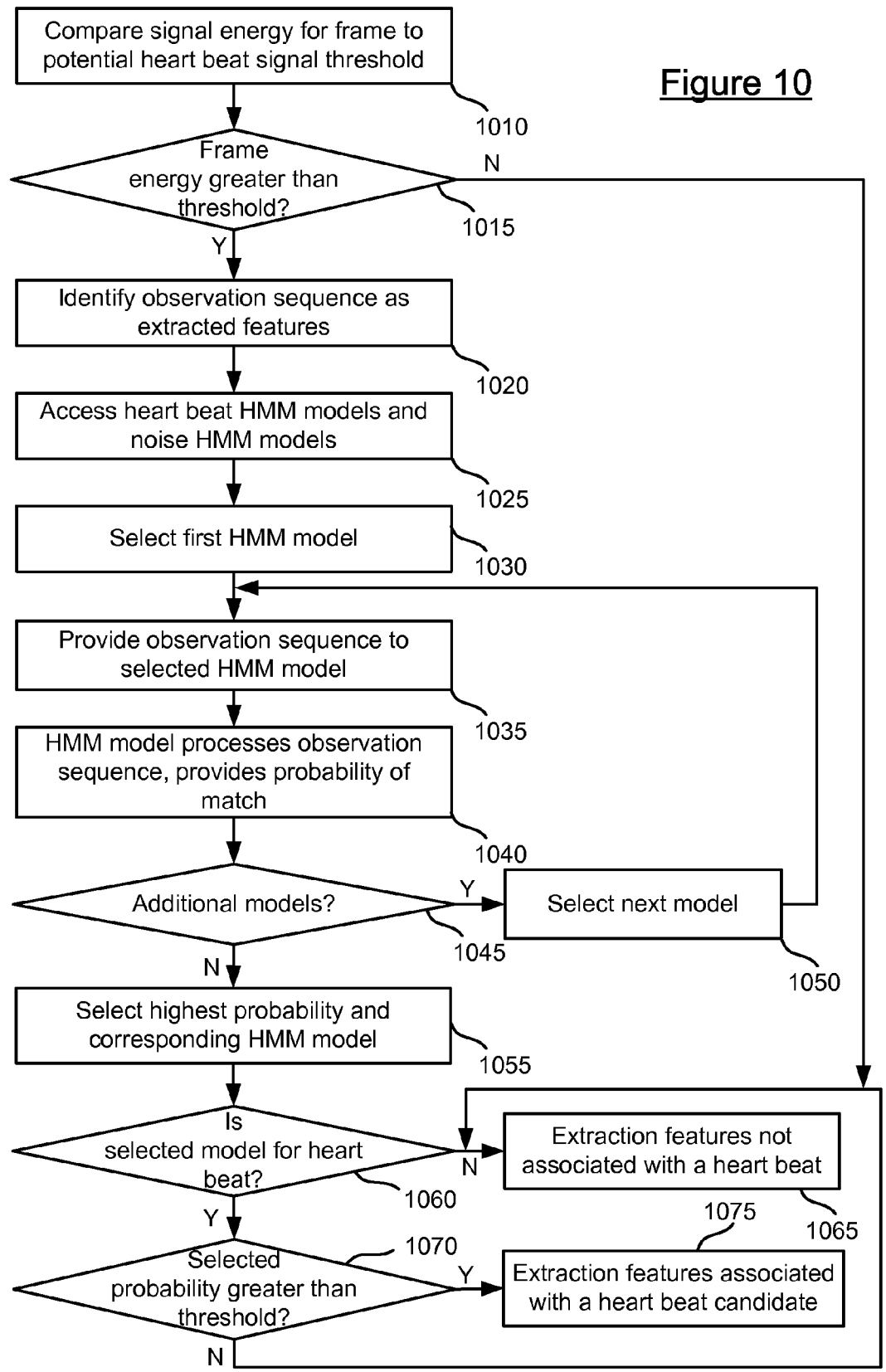
FIG. 10 is a flowchart of an embodiment of a method for performing pattern classification using a discrete Hidden Markov Model.
Figure 11:
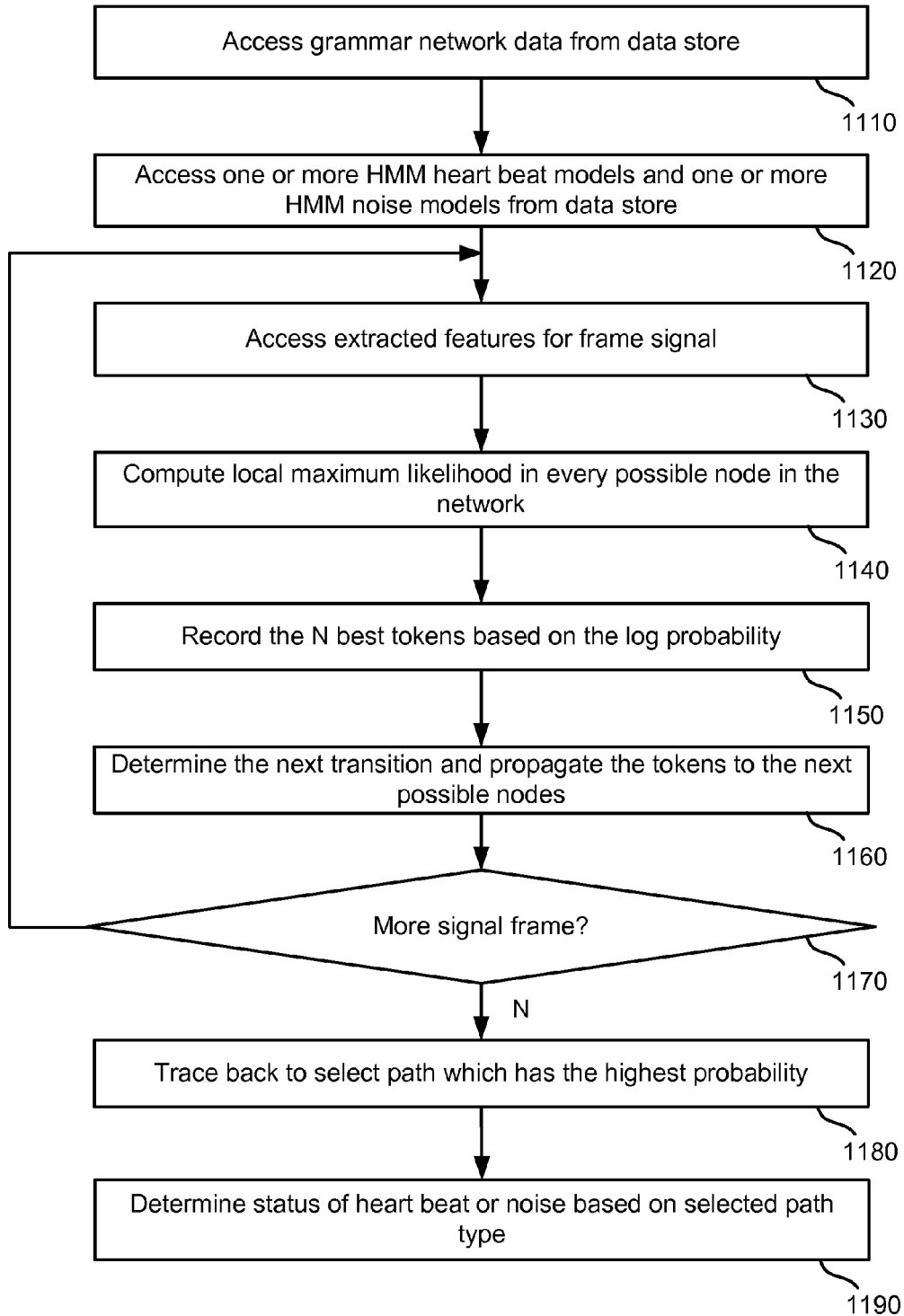
FIG. 11 is a flowchart of an embodiment of a method for performing pattern classification using continuous Hidden Markov Model.

Each of FIGS. 9-11 illustrate a method for performing pattern classification and provide more detail for step 620 of the method of FIG. 6. The methods discussed with respect to FIGS. 9-11 are intended to illustrate examples of pattern classification only, and other it is intended that other methods of pattern classification may be used to recognize a heart beat as well.

FIG. 9 is a flowchart of an embodiment of a method for performing pattern classification using feature templates and provides more detail for step 620 of the method of FIG. 6. The feature template technique involves comparing the extracted set of features to several templates of features for both heart beats and noise. The closest template to the extracted features is selected, and the extracted features are identified as either a heart beat candidate or noise based on the type of template selected.

First, the signal energy for the frame being processed is compared to a heart beat energy threshold at step 905. The threshold value may be stored in data store 316 of micro-controller 310. The threshold is set to prevent frames having only noise from being processed. In some embodiments, the heart beat threshold is set at a level such that signal energy of a heart beat will meet the threshold but noise in a signal frame without a heart beat will not meet the threshold. In some embodiments, the threshold may be set dynamically based on the average noise energy level for a period of time, such as the average noise energy over the last ten seconds of the received signal. This method of dynamic thresholding may be used to adjust the threshold based on changes detected in the signal over time. In some embodiments, other periods may be used to set the threshold as well, whether based on time, number of heart beats, or some other factor.

A determination is made as to whether the frame energy is greater than the threshold at step 910. If the frame energy is not greater than the threshold, and the method of FIG. 9 continues to step 965 where it is determined that the set of extracted features are not associated with a heart beat. The method of FIG. 6 would then end at step 620 without performing post processing and not updating the heart rate based on the signal frame data of the current frame. If the frame energy is greater than the threshold, than the signal frame data has the potential to be a heart beat (though it is not considered a true heart beat or even a heart beat candidate yet) and the method of FIG. 9 continues to step 920.

The extracted features for the current frame are accessed at step 920. In some embodiments, the features may be retrieved from data store 316, micro-controller 310 or some other source from which there were stored as a result of step 610 of the method of FIG. 6. Stored feature templates are then accessed at step 925. The accessed feature templates may include heart beat feature templates 403 and noise feature templates 404 stored in data store 316. The first accessed template is selected at step 930. The template may be either a noise or heart beat template.

The spectral difference is computed between the set of features extracted from the frame signal data and the selected template at step 935. In some embodiments, a spectral distortion or spectral-distance may be determined as a result of the comparison. The spectral difference computed for the selected template is then stored at step 940.

In some embodiments, the extracted feature sequence may have a different period (or number of frames) than the feature template. For example, the feature template may have a duration of 6 frames and the extracted feature sequence may have a duration of 5 frames. In this case, a programming method, such as a dynamic time warping (DTW) technique, can be used to measure the dissimilarity between the extracted feature sequence and template having different durations.

If more than one value for a set of extracted features is compared to determine the spectral difference, the total difference is determined for all the comparisons. Additionally, if other extracted features are compared, the total difference between all the comparisons is determined. In some embodiments, some features may be weighted to place a higher or lower emphasis on those particular features in the overall difference determination.

A determination is made as to whether there are more templates to compare at step 945. If additional templates exist to be compared to the accessed set of extracted features, the next template is selected at step 950 and the method continues to step 935. The additional templates may be associated with heart beat or noise templates. If not additional templates exist to be compared, the method of FIG. 9 continues to step 955.

The smallest total difference (or distortion or spectral-distance) is selected and the feature template corresponding to the selected difference at step 955. A determination is then made as to whether the template associated with the smallest difference represents a heart beat or noise at step 960. If the selected template is associated with noise, the extracted features for the frame signal are considered noise as well and determined not to be associated with a heart beat at step 965. If the template associated with the smallest difference is associated with heart beat, a determination is made as to whether the selected difference meets a difference threshold at step 970. The difference threshold sets a maximum value for which a selected minimum difference must comply. If the selected difference exceeds the maximum difference threshold, the method of FIG. 9 continues to step 965 where the frame signal data is determined not to be associated with a heart beat. If the selected difference does not exceed the maximum difference threshold, the signal frame data from which the set of features are extracted from is determined to be a heart beat candidate at step 975. The signal frame data is not considered to contain a heart beat until post-processing is performed during step 630 of the method of FIG. 6.

At step 965 of the method of FIG. 9, the signal frame data is determined not to be associated with a heart beat and the processing of the signal frame data with respect to feature template pattern classification ends. In some embodiments, the extracted features may be processed further according to another pattern classification technique such as a discrete HMM technique and/or continuous HMM techniques and the results of those techniques will apply as to the determination of whether the signal frame data is heart beat candidate. In some embodiments, results from all three techniques may be considered, either equally or with weighted results.

FIG. 10 is a flowchart of an embodiment of a method for performing pattern classification using a discrete HMM technique and provides more detail for step 620 of the method of FIG. 6. The discrete HMM technique involves identifying the extracted features as an observation sequence and processing the observation sequence by a number of noise HMM models and heart beat HMM models. Each model will output a probability of match for the given observation sequence. The highest probability of match is selected and the extracted features are identified as either a heart beat candidate or noise based on the HMM model associated with the selected probability.

First, the signal energy for the frame being processed is compared to a heart beat energy threshold at step 1005. The threshold value may be stored in data store 316 of microcontroller 310. This threshold of step 1005 may be the same threshold as that discussed with respect to step 905 of the method of FIG. 9. The heart beat threshold is set so that a heart beat signal energy will meet the threshold but signal frame noise without a heart beat will not.

A determination is made as to whether the frame energy is greater than the threshold at step 1010. If the frame energy is not greater than the threshold, and the method of FIG. 10 continues to step 1065 where it is determined that the set of extracted features are not associated with a heart beat. If the frame energy is greater than the threshold, than the signal frame data has the potential to be a heart beat and the method of FIG. 10 continues to step 1020.

The extracted features for the current frame are identified as an observation sequence at 1020. In some embodiments, the entire set of extracted features may be identified as an observation sequence. In some embodiments, a subset of all extracted features is selected as the observation sequence. Heart beat HMM models and noise HMM models are accessed from heart beat models 401 and noise models 402 of data store 316 at step 1025. As discussed above, each heart beat model may consist of two symbols. A first symbol may represent the flow of blood through a blood vessel and/or the expansion of the blood vessel due to a heart beat. The second symbol may represent the backflow of blood through the blood vessel and/or the contraction of a blood vessel after a heart beat. However, if the muscle mass moves at high speed during exercising, the pattern of backflow may not be recognized. Thus, in some embodiments, just one symbol may be used for a heart beat model. In some embodiments, some other number of symbols may be used in a heart beat model.

A first model of the accessed models is selected at step 1030 and the observation sequence is provided to the selected model at step 1035. In some embodiments, providing the observation sequence to the model includes providing the observation sequence to pattern classification module 314. The selected model is then used to process the observation sequence and provide a probability of match at step 1040.

In some embodiments, the heartbeat and noise models may be implemented as Hidden Markov Models (HMMs). For example, a "left to right" HMM may be used to recognize a heart beat and/or noise element within a heart beat. The HMM models may each be characterized by the number of states in the model N, the number of observation symbols per state M, the state transition probability A, observation symbol probability distribution B and the initial state distribution $\pi$.

The number of states N in the heartbeat models may vary depending on the number of models and the system used to process the models. In some embodiments, the number of states N for each heat beat and noise HMM model is seven. In some embodiments, a heart beat HMM model having two symbols may have five states for each symbol, for a total of ten states not including the start and end states. The number of observation symbols M per state may be the number of frame signal features, such as cepstral coefficients, formants, energy, heartbeat duration and other values. In some embodiments, the number of observation symbols may be between 13 and 39. In some embodiments, the number of observation symbols may be between 20 and 26.

The state transition probability is the probability that one state will transition to another particular state, and can be expressed as $A=\{a_{ij}\}$, where $a_{ij}=P\ [q_t+1=S_j|q_t=S_i]$, where i and j have values between 1 and N. When a "left to right" HMM is used, the corresponding transition matrix is a diagonal matrix. An example of a diagonal matrix of state transition probability is below:

$$\begin{Bmatrix} 0 & 1.0e+00 & 0 & 0 & 0 & 0 & 0 \\ 0 & 5.4e-01 & 4.6e-01 & 0 & 0 & 0 & 0 \\ 0 & 0 & 5.0e-01 & 4.9e-01 & 0 & 0 & 0 \\ 0 & 0 & 0 & 5.5e-01 & 4.5e-01 & 0 & 0 \\ 0 & 0 & 0 & 0 & 7.4e-03 & 9.9e-01 & 0 \\ 0 & 0 & 0 & 0 & 0 & 1.0e-01 & 8.9e-0 \\ 0 & 0 & 0 & 0 & 0 & 0 & 0 \end{Bmatrix}$$

In some embodiments, the observation symbol probability distribution B may be represented by the function $B=\{b_j(k)\}$, where $b_j(k)=P\ [v_k\ at\ t|q_t=S_j]$, where j has values between 1 and N and K has values between 1 and M. An observation symbol probability distribution B for a heart beat model can be described by the example three Gaussian mixture as below:

```
<STATE> 2 <-- state#2
<NUMMIXES> 3 <-- 3 Gaussian mixture
<MIXTURE> 1 1.614997e-001 <-- mixture 1 with weighting
<MEAN> 26 <-- the input feature has 26 dimensions
```

| | | | | |
|---|---|---|---|---|
| -7.335623e+000 | -5.524750e-001 | 6.083916e+000 | 6.682457e+000 | 5.829988e+000 |
| 4.552678e+000 | 3.053185e+000 | 3.594296e+000 | 3.472806e+000 | 2.778500e+000 |
| 2.344059e+000 | 2.076142e+000 | 4.012048e-001 | -2.234675e-001 | -6.913625e-002 |
| 3.859574e-001 | 3.646993e-001 | 1.885375e-001 | -3.184729e-002 | 7.119856e-002 |
| 1.063162e-001 | 2.214953e-002 | -9.553448e-002 | -4.704625e-002 | 1.692603e-001 |
| 4.095135e-003 | | | | |

```
<VARIANCE> 26
```

| | | | | |
|---|---|---|---|---|
| 6.064819e+000 | 1.492445e+001 | 9.111507e+000 | 9.968517e+000 | 1.667336e+001 |
| 1.800946e+001 | 1.923933e+001 | 1.815137e+001 | 1.511338e+001 | 1.650653e+001 |
| 1.507320e+001 | 1.234248e+001 | 1.012527e-002 | 1.701336e+000 | 2.751490e+000 |
| 1.190388e+000 | 2.235020e+000 | 3.031187e+000 | 3.805880e+000 | 2.877148e+000 |
| 2.675171e+000 | 2.847878e+000 | 2.144249e+000 | 1.870771e+000 | 1.568759e+000 |
| 3.809229e-004 | | | | |

```
<GCONST> 7.653376e+001
```

-continued

```
<MIXTURE> 2 3.486372e−001
<MEAN> 26
 2.627326e+000   1.329051e+000  −1.134783e+000  −2.049442e+000  −1.899238e+000
−2.375481e+000  −1.577606e+000  −9.970551e−001  −1.018946e+000  −9.094471e−001
−1.088839e+000  −5.220632e−001   7.046627e−001   2.649817e+000  −9.975603e−002
−2.527418e+000  −2.596035e+000  −2.047962e+000  −1.748837e+000  −1.134814e+000
−9.340281e−001  −9.791703e−001  −1.019024e+000  −9.198254e−001  −7.388496e−001
 5.777986e−002
<VARIANCE> 26
 3.365233e+001   2.096466e+001   4.925962e+001   4.087632e+001   4.245908e+001
 2.797114e+001   2.214656e+001   2.314966e+001   1.902778e+001   1.962826e+001
 1.746292e+001   1.859155e+001   4.188740e−002   3.606961e+000   2.526721e+000
 6.482423e+001   3.677197e+000   4.400999e+000   2.984235e+000   2.583545e+000
 2.698042e+000   2.463989e+000   2.376609e+000   2.284329e+000   2.232023e+000
 4.166499e−003
<GCONST> 9.161729e+001
<MIXTURE> 3 4.898616e−001
<MEAN> 26
 8.535575e−001  −3.870160e+000  −1.245709e+000   1.379836e+000   1.594710e+000
 1.101780e+000   1.092654e+000  −3.312795e−002  −1.032832e+000  −1.238943e+000
−1.211667e+000  −1.297268e+000   8.864919e−001  −1.312104e+000  −2.457915e+000
 4.271719e−001   9.468748e−001   5.694487e−001   1.358161e−001   5.225847e−002
−2.966875e−001  −5.288242e−001  −5.928908e−001  −2.515194e−001  −5.109842e−001
 3.681988e−002
<VARIANCE> 26
 4.067065e+000   1.798957e+001   1.465096e+001   1.027467e+001   1.124570e+001
 1.596379e+001   1.475497e+001   1.724740e+001   1.767445e+001   1.726367e+001
 1.335523e+001   1.426660e+001   5.071117e−003   5.552661e−001   1.568640e+000
 2.260648e+000   1.321402e+000   1.713235e+000   2.117280e+000   1.894006e+000
 2.028143e+000   2.036679e+000   2.062976e+000   1.825414e+000   1.773973e+000
 3.851150e−004
```

The initial state distribution π may be represented as $\{\pi_i\}$, where $\pi_i = P[q_i = s_j]$, where i has values equal to and between 1 and N.

In some embodiments, the HMM model generates a probability for each observation sequence value. In this case, the generated probabilities are multiplied together and stored for the observation sequence as part of step 1040. For example, if the probabilities for matching a selected model were [0.8, 0.78, 0.93, 0.9, 0.84, 0.87, 0.91], the total probability would be the produce of all the individual values, or 0.347. The total probability is stored within micro-controller 310, data store 316 or some other memory location.

The above examples are merely one example of each of a state transition probability calculation and observation symbol probability calculation. Other calculation methods and data, including that used for two or more symbols in an HMM model, are possible and intended to be within the scope of the present technology.

A determination is made as to whether there are more models to compare to the observation sequence at step 1045. If additional models exist to be compared to the observation sequence, the next model is selected at step 1050 and the method returns to step 1035. The additional models may be associated with either heart beat, noise models or both. If no additional models exist to be compared, the method of FIG. 10 continues to step 1055.

The highest total probability generated at step 1040 for the different HMM models and HMM model corresponding to the highest probability are selected at step 1055. A determination is then made as to whether the selected HMM model associated with the highest probability represents a heart beat or noise at step 1060. If the selected model is associated with noise, the frame signal data and extracted features for the observation sequence is considered noise and is determined not to contain a heart beat at step 1065. If the HMM model associated with the highest probability is associated with heart beat, a determination is made as to whether the selected probability meets a probability threshold at step 1070. The probability threshold sets a minimum value for which a selected probability must comply. If the selected probability is less than the minimum probability threshold, the method of FIG. 10 continues to step 1065 where the frame signal data is determined not to be associated with a heart beat. If the selected probability does is greater than the minimum probability threshold, the signal frame data from for the observation sequence is determined to be a heart beat candidate at step 1075. As with the method of FIG. 9, the signal frame data is not considered to contain a heart beat until post-processing is performed during step 630 of the method of FIG. 6.

FIG. 11 is a flowchart of an embodiment of a method for performing pattern classification using continuous Hidden Markov Models. In particular, the flow chart of FIG. 11 illustrates a method for implementing the Viterbi algorithm to perform pattern classification using continuous HMM models, a grammar network, and observation features from a signal being processed and provides more detail for step 620 of the method of FIG. 6. The Viterbi algorithm and continuous HMM technique involves continuously identifying extracted features as an observation sequence, determining a most likely state sequence from the observation sequence, and determining the most probably match between the most likely state sequence and several HMM. The highest probability of match is selected and the extracted features are identified as either a heart beat candidate or noise based on the HMM model associated with the selected probability.

First, a grammar network is accessed from data store 316 at step 1110. The grammar network defines the allowable state sequences semantically. A generated state sequence from the Viterbi search may not be a valid sequence without the constraints of the grammar network. In some embodiment, the grammar network is defined as below: [sil] {M1|M2| M3| . . . } [sil], where 'M' represents a heart beat or a noise model. For example, a first heart beat pattern may be represented as <M1, M2>, a second heart beat pattern as <M3, M4, M5> and a noise pattern as <M6>. Thus, an allowable state sequence may be comprised of one or more heart rate models, one or more noise models, or a combination of both. Each HMM model may have an observation sequence which is associated with a state sequence, wherein one observation feature transition corresponds to a state transition.

The recognition process is performed as follows. First, one or more HMM heart rate models and one or more HMM noise models are accessed from data store 316 at step 1120. After accessing the models, features are extracted for a frame signal at step 1130. In some embodiments, step 1130 of the method of FIG. 11 may overlap or include feature extraction performed at step 610 of the method of FIG. 6. As the method of FIG. 6 is performed recursively, the feature extraction is performed repeatedly.

A local maximum likelihood is computed in every possible node in the grammar network at step 1140. Thus, for a received signal having T number of frames, every path from the start node to the exit node of the grammar network which passes through exactly T emitting HMM states is a potential recognition hypothesis. Each of these paths has a log probability which is computed by summing the log probability of each individual transition in the path and the log probability of each emitting state which generates the corresponding observation.

Next, the N best tokens are recorded based on the log probability at step 1150. The next transition is then determined and the tokens are propagated to the next possible nodes at step 1160. The search algorithm is to find those paths through the network which have the highest log probability. These paths are found using a Token Passing algorithm. A token represents a partial path through the network extending from time 0 through to time t. At time 0, a token is placed in every possible start node.

At each time step, tokens are propagated along connecting transitions stopping whenever they reach an emitting HMM state. When there are multiple exits from a node, the token is copied so that all possible paths are explored in parallel. As the token passes across transitions and through nodes, its log probability is incremented by the corresponding transition and emission probabilities. A network node can hold at most N tokens. Hence, at the end of each time step, all but the N best tokens in any node are discarded. As each token passes through the network it must maintain a history recording its route. The history includes the model sequence and the time of each model to model transition. Normally, N=1 is sufficient for most cases.

A determination is then made as to whether more signal frame exists to process at step 1170. In some embodiments, step 1170 is optional, for example when the frame signal is continually processed until the monitoring is stopped. If a further portion of the signal exists to be processed, features are extracted from the frame signal portion at step 1130. If no further portion of the signal exists to be processed, the system traces back through the network to select a path having the highest probability at step 1180. A status of heart beat or noise is then determined for the frame based on the selected path having the highest probability at step 1190.

Figure 12:
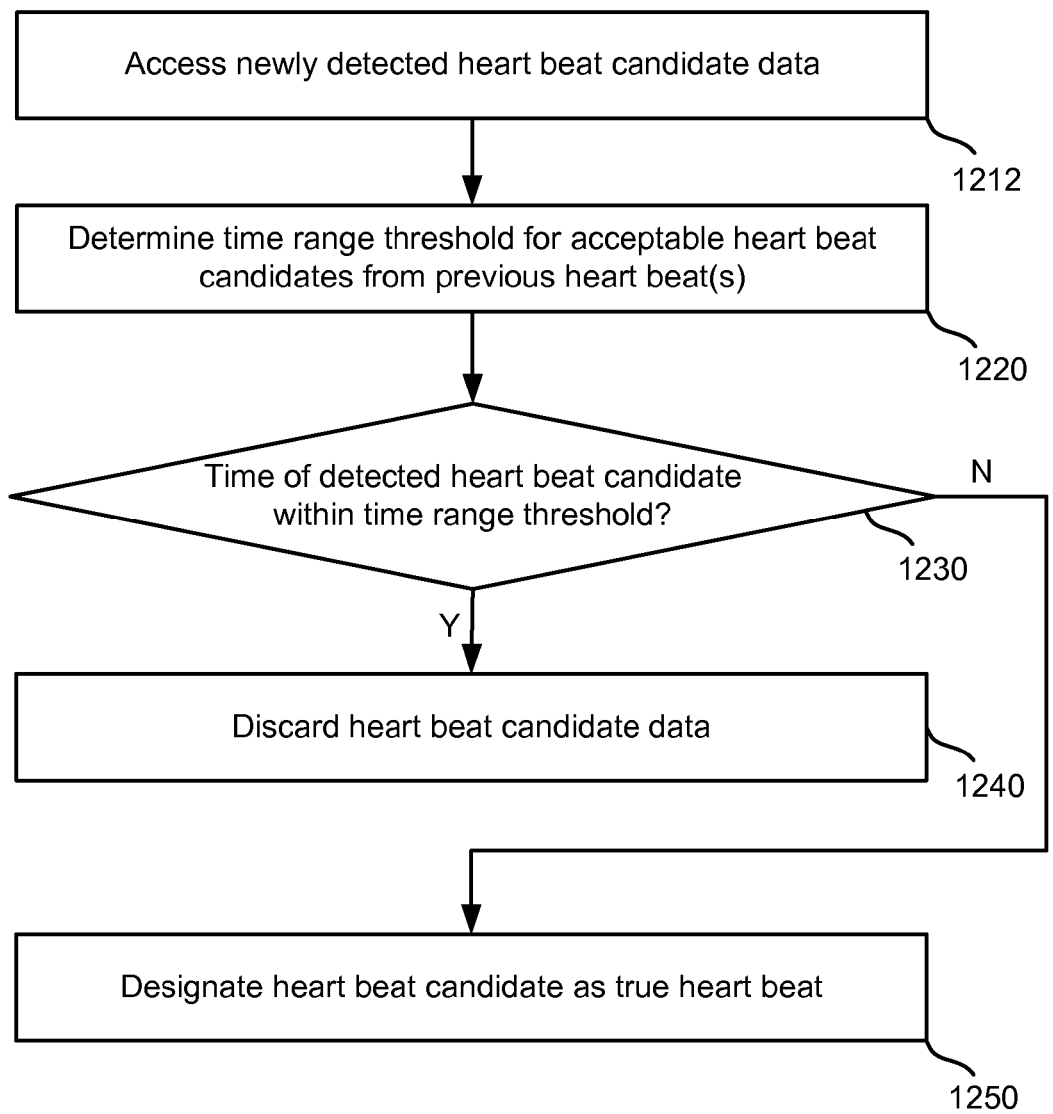
FIG. 12 is a flowchart of an embodiment of a process for performing post processing on a heartbeat candidate signal.

FIG. 12 is a flowchart of an embodiment of a method for performing post-processing on a heartbeat candidate signal. In some embodiments, the method of FIG. 12 provides more detail for step 630 of the method of FIG. 6. First, data associated with a newly detected heartbeat candidate is accessed at step 1210. In some embodiments, the heart beat candidate data is the frame signal data which has been determined to have a highest probability match with a heart beat model. Next, the time range threshold for an acceptable heartbeat candidate is determined from the previous heartbeats at step 1220. As discussed above, the time range threshold for an acceptable heartbeat candidate may comprise a threshold for which acceptable changes of a heartbeat may occur. The threshold may be based on a stored value, the current heart rate, or generated in some other manner. For example, if the current heart rate of the subject is 170 beats per minute, this would correspond to 2.85 beats per second, or one beat every 0.35 seconds. In some embodiments, a threshold may be set at plus or minus twenty percent of the current heart rate, to provide a practical limit for filtering out sounds that are very unlikely to be a heartbeat due to the known current heart rate and physiological limitations of the heart in increasing and decreasing in heart rate. In some embodiments, heart beat candidates that are detected too soon (or too late) that are unlikely to be a valid heart beat because the subject's heart can't operate at such a fast (or slow) frequency may also be used to set thresholds.

A determination is made as to whether the time of the detected heartbeat candidate is within the time range threshold at step 1230. If the detected heartbeat candidate is not within the time range threshold, the heartbeat candidate is discarded at step 1240. In this case, the heart beat candidate is determined not to be a legitimate heart beat. The corresponding process of FIG. 4 then ends if the heartbeat candidate is discarded at step 1240 of the flowchart of FIG. 12. If the detected heartbeat candidate is within the time range threshold, the heartbeat candidate is designated as a true heart beat at step 1250.

In some embodiments, the heart beat models used to determine the probability of match with the detected heart beats may be trained to provide a more effective comparison. The models may be used in the HMM probability determination or in some other probability matching process. To develop the heart beat models, heart beat features are developed from a sampling of several different subjects. Each subject in the sampling group may each have different biological and other characteristics. For example, the heart beat subjects may have a variety of ages, ranging from early tens to people in their seventies or older. The sampling group may also include both male and female subjects. Additionally, the sampling group may have specific heart beat characteristics, such as an irregular heart beat, different back flow, and other characteristics. The larger the number of heart beat models used, the higher the probability of recognizing a legitimate heart beat.

In some embodiments, the size of a wrist-worn heart beat monitor makes processing and storage resource usage very important. Thus, it may be desired to minimize the number of heart beat models to a smaller amount. In any case, it can be valuable to train the heart beat models, such as HMM models, by re-estimating the HMM parameters associated with each model. The HMM model training or parameter re-estimation may be done reiteratively by evaluating the models for heart beats with different characteristics. This enables the heart beat models to be most effective in determining the probability of a match with heart beat candidates detected from a subject.

The foregoing detailed description of the technology herein has been presented for purposes of illustration and description. It is not intended to be exhaustive or to limit the technology to the precise form disclosed. Many modifications and variations are possible in light of the above teaching. The described embodiments were chosen in order to best explain the principles of the technology and its practical application to thereby enable others skilled in the art to best utilize the technology in various embodiments and with various modifications as are suited to the particular use contemplated. It is intended that the scope of the technology be defined by the claims appended hereto.

We claim:

1. A computer implemented method to determine a heart rate for a subject, comprising:
    detecting a heartbeat signal from the subject;
    extracting a set of two or more types of heartbeat features from the heartbeat signal;
    accessing, from stored data, one or more heartbeat patterns and one or more noise patterns, the one or more heartbeat patterns comprising at least one of:
    (a) one or more heartbeat models and (b) one or more heartbeat templates, and the one or more noise patterns comprising at least one of: (c) one or more noise models and (d) one or more noise templates;
    determining whether the set of two or more types of heartbeat features more closely matches the one or more heartbeat patterns or the one or more noise patterns;
    if the set of two or more types of heartbeat features more closely matches the one or more noise patterns, determining that the set of two or more types of heartbeat features is not to be used to update the heart rate for the subject; if the set of two or more types of heartbeat features more closely matches the one or more heartbeat patterns, determining that the set of two or more types of heartbeat features represents a heartbeat candidate;
    performing post-processing to determine that the heartbeat candidate represents a heartbeat; and
    updating the heart rate for the subject based on timing of the heartbeat.

2. The computer implemented method of claim 1, wherein the heartbeat signal is detected within an ultrasound signal reflected from the subject.

3. The computer implemented method of claim 1, wherein said extracting includes:
    dividing the heartbeat signal into one or more frames; and
    extracting the set of two or more types of heartbeat features in each frame of the heartbeat signal.

4. The computer implemented method if claim 1, wherein:
    the two or more types of heartbeat features comprise one or more of signal energy values, heartbeat duration values and delta features.

5. The computer implemented method of claim 4, further comprising:
    calculating the delta features based on differences among heartbeat features of the heartbeat signal.

6. The computer implemented method of claim 1, wherein said extracting includes:
    performing linear predictive coding analysis on the heartbeat signal to determine a set of linear predictive coding coefficients.

7. The computer implemented method of claim 6, wherein said extracting includes:
    performing cepstral analysis using the set of linear predictive coding coefficients to generate a set of cepstral coefficients.

8. The computer implemented method of claim 7, wherein said extracting includes extracting Mel Frequency Cepstral Coefficients.

9. The computer implemented method of claim 7, wherein said extracting includes:
    estimating one or more formants of the heartbeat signal based on the set of the linear predictive coding coefficients.

10. The computer implemented method of claim 9, wherein the two or more types of heartbeat features include cepstral coefficients, the method further comprising:
    weighting the cepstral coefficients.

11. The computer implemented method of claim 7, further comprising:
    weighting a subset of the set of two or more types of features.

12. The computer implemented method of claim 1, wherein:
    the one or more heartbeat models and the one or more noise models are part of at least one grammar network which defines multiple states and allowable sequences of the states, each state has an associated probability of transitioning to other states of the multiple states; and
    the determining whether the set of two or more types of heartbeat features more closely matches the one or more heart beat patterns or the one or more noise patterns comprises determining a most probable sequence of the states, among the allowable sequences of the states, which is associated with the set of two or more types of heartbeat features.

13. The computer implemented method of claim 12, wherein:
    the determining the most probable sequence of the states uses Hidden Markov Model techniques.

14. The computer implemented method of claim 1, wherein each of the one or more noise models represents noise generated from at least one of muscle movement and body movement.

15. The computer implemented method of claim 1, wherein:
    the determining whether the set of two or more types of heartbeat features more closely matches the one or more heartbeat patterns or the one or more noise patterns comprises determining whether a probability of a match is higher between: (a) the one or more heartbeat models and the set of two or more types of heartbeat features or (b) the one or more noise models and the set of two or more types of heartbeat features.

16. The computer implemented method of claim 1, wherein:
    the determining whether the set of two or more types of heartbeat features more closely matches the one or more heartbeat patterns or the one or more noise patterns comprises determining whether a similarity of a match is higher between: (a) the one or more heartbeat templates and the set of two or more types of heartbeat features or (b) the one or more noise templates and the set of two or more types of heartbeat features.

17. The computer implemented method of claim 1, wherein the one or more heartbeat models has at least first and second symbols, and each symbol characterizes a basic heartbeat signal pattern.

18. The computer implemented method of claim 17, wherein the first symbol is derived from a first heartbeat pattern associated with a heart contraction and the second symbol is derived from a second heartbeat pattern associated with vessel backflow.

19. The computer implemented method of claim 1, wherein the one or more heartbeat models are trained using a sampling of subjects having different ages and genders.

20. The computer implemented method of claim 1, wherein the one or more heartbeat models are trained using a sampling of subjects having different heartbeat back flow characteristics.

21. The computer implemented method of claim 1, wherein the one or more heartbeat models are trained using a sampling of subjects including a subject having an irregular heartbeat.

22. The computer implemented method if claim 1, wherein:
the two or more types of heartbeat features includes at least one of linear predictive coding coefficients, cepstrum coefficients, mel-frequency cepstrum coefficients, perceptual linear prediction coefficients, formants, signal energy, signal duration and cepstrum coefficient differences.

23. The computer implemented method if claim 1, wherein:
the one or more noise patterns comprise multiple noise patterns.

24. The computer implemented method if claim 1, further comprising:
determining a probability that the set of two or more types of heartbeat features is most likely characterized by more closely matches the one or more heartbeat models; and
determining whether the probability exceeds a threshold, the determining that identifying the set of two or more types of heartbeat features represents as representing the heartbeat candidate requires the probability to exceed the threshold.

25. The computer implemented method if claim 1, wherein:
the post-processing determines that the heartbeat candidate represents the heartbeat by determining that a time of the heartbeat candidate is within a time range threshold relative to one or more previous heartbeats.

26. The computer implemented method of claim 1, wherein:
the updating the heart rate for the subject includes transmitting the heart rate to a display device.

27. One or more processor readable storage devices having processor readable code embodied on said processor readable storage devices, said processor readable code for programming one or more processors to perform a method to determine a heart rate for a subject, the method performed comprising:
extracting a set of features from each frame of a plurality of frames of a heartbeat signal of the subject;
performing pattern classification of the set of features using one or more heartbeat patterns and one or more noise patterns, the one or more heartbeat patterns comprising at least one of: (a) one or more heartbeat models and (b) one or more heartbeat templates, and the one or more noise patterns comprising at least one of: (c) one or more noise models and (d) one or more noise templates;
determining whether the set of features more closely matches the one or more heartbeat patterns or the one or more noise patterns, based on the performing pattern classification;
if the set of features more closely matches the one or more noise patterns, determining that the set of features is not to be used to update the heart rate for the subject;
if the set of features more closely matches the one or more heartbeat patterns, determining that the set of features represents a heartbeat candidate;
performing post-processing to determine whether the heartbeat candidate represents a heartbeat; and
updating the heart rate for the subject based on timing of the heartbeat, if the post-processing determines that the heartbeat candidate represents the heartbeat.

28. The one or more processor readable storage devices of claim 27, wherein said extracting includes:
receiving a signal reflected from an artery of the subject;
dividing the reflected signal into frames; and
extracting the set of features for a portion of the reflected signal within each frame.

29. The one or more processor readable storage devices of claim 27, wherein the set of features includes at least one of linear predictive coding coefficients, cepstrum coefficients, mel-frequency cepstrum coefficients, perceptual linear prediction coefficients, formants, signal energy, signal duration and delta features.

30. The one or more processor readable storage devices of claim 27, wherein said performing pattern classification includes:
accessing one or more heartbeat models which characterize the one or more heartbeat patterns;
accessing one or more noise models which characterize the one or more noise patterns;
accessing at least one grammar network which defines multiple states and allowable sequences of the states, each state has an associated probability of transitioning to other states of the multiple states; and
using a Viterbi search algorithm to find a most likely sequence of the states through the at least one grammar network based on the set of features, wherein:
the set of features is determined to represent the heartbeat candidate if the most likely sequence of the states is associated with the one or more heartbeat models; and
the set of features is determined to not be used in updating the heart rate for the subject represent the noise if the most likely sequence of the states is associated with the one or more noise models.

31. The one or more processor readable storage devices of claim 27, wherein said performing pattern classification includes:
accessing one or more heartbeat models which characterize the one or more heartbeat patterns;
accessing one or more noise models which characterize the one or more noise patterns;
accessing at least one grammar network which defines multiple states and sequences of the states, each state has an associated probability of transitioning to other states of the multiple states;
processing each value in an observation sequence against each state in each heartbeat model and noise model; and
generating a total probability of match for each model by multiplying the probability of each value together for each model.

32. The one or more processor readable storage devices of claim 27, wherein said performing pattern classification includes:
accessing one or more heartbeat templates which characterize the one or more heartbeat patterns; and
generating a similarity measure of the set of features against each of the heartbeat templates using a dynamic time warping algorithm.

33. The one or more processor readable storage devices of claim 27, wherein said determining whether the set of features more closely matches the one or more heartbeat patterns or the one or more noise patterns includes:
determining the subject's heart rate based on a matched model, selected probability or selected similarity.

34. The one or more processor readable storage devices of claim 27, wherein said step of performing pattern classification includes:
determining if a probability of a match is higher between: (a) the one or more heartbeat patterns and the set of features, and or (b) the one or more noise patterns and the set of features; and determining if the probability of a match exceeds a threshold value; and the post-processing determines determining that the heartbeat candidate does not represent the heartbeat set of features represents the noise if the probability of a match does not exceed the threshold value, even if the probability of a match is higher between the one or more heartbeat patterns and the set of features than between the one or more noise patterns and the set of features.

35. The one or more processor readable storage devices of claim 27, wherein:
the one or more noise patterns comprise multiple noise patterns.

36. A heart rate monitor, comprising:
at least one transducer which detects a heartbeat signal from a subject;
at least one microcontroller associated with the at least one transducer;
at least one data store associated with the microcontroller, the data store comprising one or more heartbeat patterns and one or more noise patterns, the one or more heartbeat patterns comprising at least one of: (a) one or more heartbeat models and (b) one or more heartbeat templates, and the one or more noise patterns comprising at least one of: (c) one or more noise models and (d) one or more noise templates; and
an amplifier and a demodulator arranged between the at least one transducer and the at least one microcontroller;
the at least one microcontroller: (i) extracts a set of two or more types of heartbeat features from the heartbeat signal, (ii) accesses, from the at least one data store, the one or more heartbeat patterns and one or more noise patterns, (iii) determines whether the set of two or more types of heartbeat features more closely matches the one or more heartbeat patterns or the one or more noise patterns, (iv) if the set of two or more types of heartbeat features more closely matches the one or more noise patterns, determines that the set of two or more types of heartbeat features is not to be used to update a heart rate for a subject, (v) if the set of two or more types of heartbeat features more closely matches the one or more heartbeat patterns, determines that the set of two or more types of heartbeat features represents a heartbeat candidate, and (iv) updates the heart rate for the subject based on timing of the heartbeat candidate.

37. The heart rate monitor of claim 36, further comprising:
a local display associated with the at least one microcontroller which displays the heart rate.

38. The heart rate monitor of claim 36, further comprising:
a transmitter associated with the at least one microcontroller, the transmitter transmits the heart rate in a wireless signal to a receiver of a remote display.

39. The heart rate monitor of claim 36, wherein:
the at least one transducer detects the heartbeat signal within an ultrasound signal reflected from the subject.

40. A heart rate monitor, comprising:
at least one transducer which detects a heartbeat signal from a subject;
at least one microcontroller associated with the at least one transducer; and
at least one data store associated with the microcontroller, the data store comprising one or more heartbeat patterns and one or more noise patterns, the one or more heartbeat patterns comprising at least one of: (a) one or more heartbeat models and (b) one or more heartbeat templates, and the one or more noise patterns comprising at least one of: (c) one or more noise models and (d) one or more noise templates;
the at least one microcontroller: (i) extracts a set of heartbeat features from the heartbeat signal, (ii) accesses, from the at least one data store, the one or more heartbeat patterns and one or more noise patterns, (iii) determines whether the set of features more closely matches the one or more heartbeat patterns or the one or more noise patterns, (iv) if the set of features more closely matches the one or more noise patterns, determines that the set of features is not to be used to update a heart rate for a subject, (v) if the set of features more closely matches the one or more heartbeat patterns, determines that the set of features represents a heartbeat candidate, and (vi) updates the heart rate for the subject based on timing of the heartbeat candidate.

41. The heart rate monitor of claim 40, wherein:
the at least one transducer detects the heartbeat signal within an ultrasound signal reflected from the subject.

\* \* \* \* \*